(12) United States Patent
Clas et al.

(10) Patent No.: US 8,552,193 B2
(45) Date of Patent: Oct. 8, 2013

(54) ALTERNATIVE FORMS OF THE PHOSPHODIESTERASE-4 INHIBITOR N-CYCLOPROPYL-1-{3-[(1-OXIDOPRYIDIN-3-YL)ETHYNYL]PHENYL}-4-OXO-1,4-DIHYDRO-1,8-NAPHTHYRIDINE-3-CARBOXYAMIDE

(75) Inventors: Sophie-Dorothee Clas, Montreal (CA); Rafik Naccache, Laval (CA); Hongshi Yu, Dollard-des-Ormeaux (CA); Jerry Murry, New York, NY (US); Narayan Vanankaval, Plainsboro, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 398 days.

(21) Appl. No.: 12/750,777

(22) Filed: Mar. 31, 2010

(65) Prior Publication Data

US 2011/0245290 A1 Oct. 6, 2011
US 2013/0231363 A9 Sep. 5, 2013

Related U.S. Application Data

(62) Division of application No. 11/547,916, filed as application No. PCT/US2005/013853 on Apr. 22, 2005, now abandoned.

(60) Provisional application No. 60/565,446, filed on Apr. 26, 2004.

(51) Int. Cl.
 *A61K 31/4375* (2006.01)
 *C07D 471/02* (2006.01)
(52) U.S. Cl.
 USPC .......................................... 546/123; 514/300
(58) Field of Classification Search
 None
 See application file for complete search history.

(56) References Cited

U.S. PATENT DOCUMENTS

2008/0119509 A1* 5/2008 Clas et al. .................... 514/300

FOREIGN PATENT DOCUMENTS

| WO | WO03001879    |   | 3/2003 |
|----|---------------|---|--------|
| WO | WO2004/048377 | * | 6/2004 |
| WO | WO2004048377  |   | 6/2004 |

OTHER PUBLICATIONS

Morissette et al. in Drug Delivery Reviews, 56 (2004) 275-300.*
H. G. Brittain et al. "Polymorphism in Pharmaceutical Solids", Marcel Dekker, Inc. Publishing, pp. 141-161, 184-185, 235-236, 1999.

* cited by examiner

*Primary Examiner* — Dennis Heyer
(74) *Attorney, Agent, or Firm* — Patricia A. Shatynski; Valerie J. Camara

(57) ABSTRACT

The present invention is directed to alternative forms of the title phosphodiesterase 4 inhibitor which has the structural formula shown immediately below:

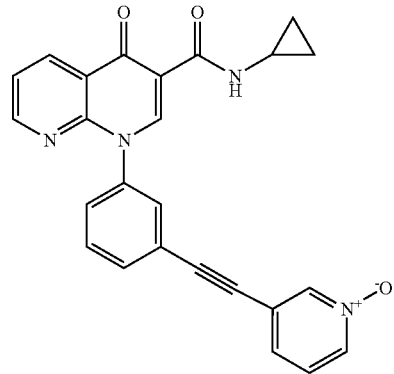

Compound IX

3 Claims, 17 Drawing Sheets

* TEMPERATURES WITH SIGNIFICANT XRPD PATTERN CHANGES

ALTERNATIVE FORMS OF THE PHOSPHODIESTERASE-4 INHIBITOR N-CYCLOPROPYL-1-{3-[(1-OXIDOPRYIDIN-3-YL)ETHYNYL]PHENYL}-4-OXO-1,4-DIHYDRO-1,8-NAPHTHYRIDINE-3-CARBOXYAMIDE

This application is a Divisional derived from U.S. application Ser. No. 11/547,916, filed on Oct. 6, 2006, now abandoned which is the U.S. National Phase application under 35 U.S.C. §371 of PCT Application No. PCT/US2005/13853, filed Apr. 22, 2005, which claims priority under 35 U.S.C. §119(e) from U.S. Provisional Application Ser. No. 60/565,446, filed Apr. 26, 2004.

BACKGROUND OF THE INVENTION

1. Field of the Invention

The present invention is directed to alternative forms of the title phosphodiesterase 4 inhibitor which has the structural formula shown immediately below:

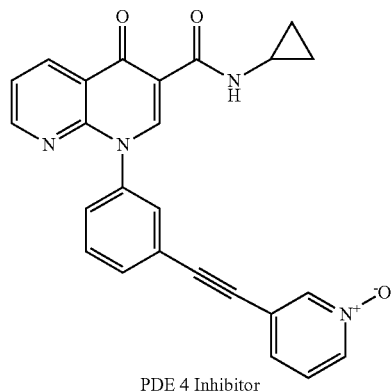

PDE 4 Inhibitor

2. Related Background

The compound is a potent inhibitor of phosphodiesterase 4, and is thereby useful in the treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues.

This compound, its utility as well as an Example describing its preparation is disclosed in WO 03/018579. See Example 9 at page 50 of the application, wherein the compound is identified by the name N-Cyclopropyl-1-[3-(3-pyridinylethynyl)phenyl]-1,4-dihydro[1,8]naphthyridin-4-one-3-carboxamide.

SUMMARY OF THE INVENTION

The present invention is directed to alternative forms of the title phosphodiesterase 4 inhibitor which has the structural formula shown immediately below:

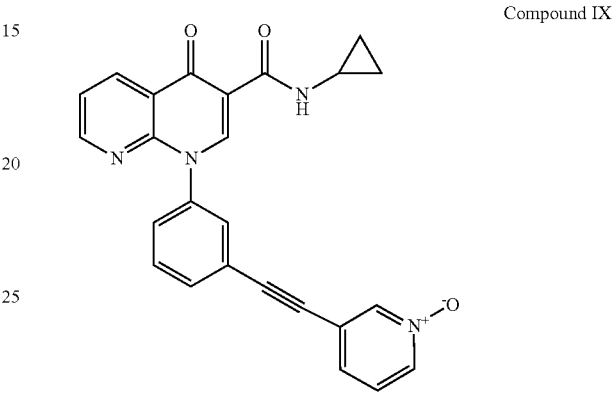

Inhibitors of phosphodiesterase-4 have been shown to be useful in the treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues.

SUMMARY OF THE DRAWINGS

The following appended drawings are referred to in this patent application.

DETAILED DESCRIPTION OF THE INVENTION

Figure 1:
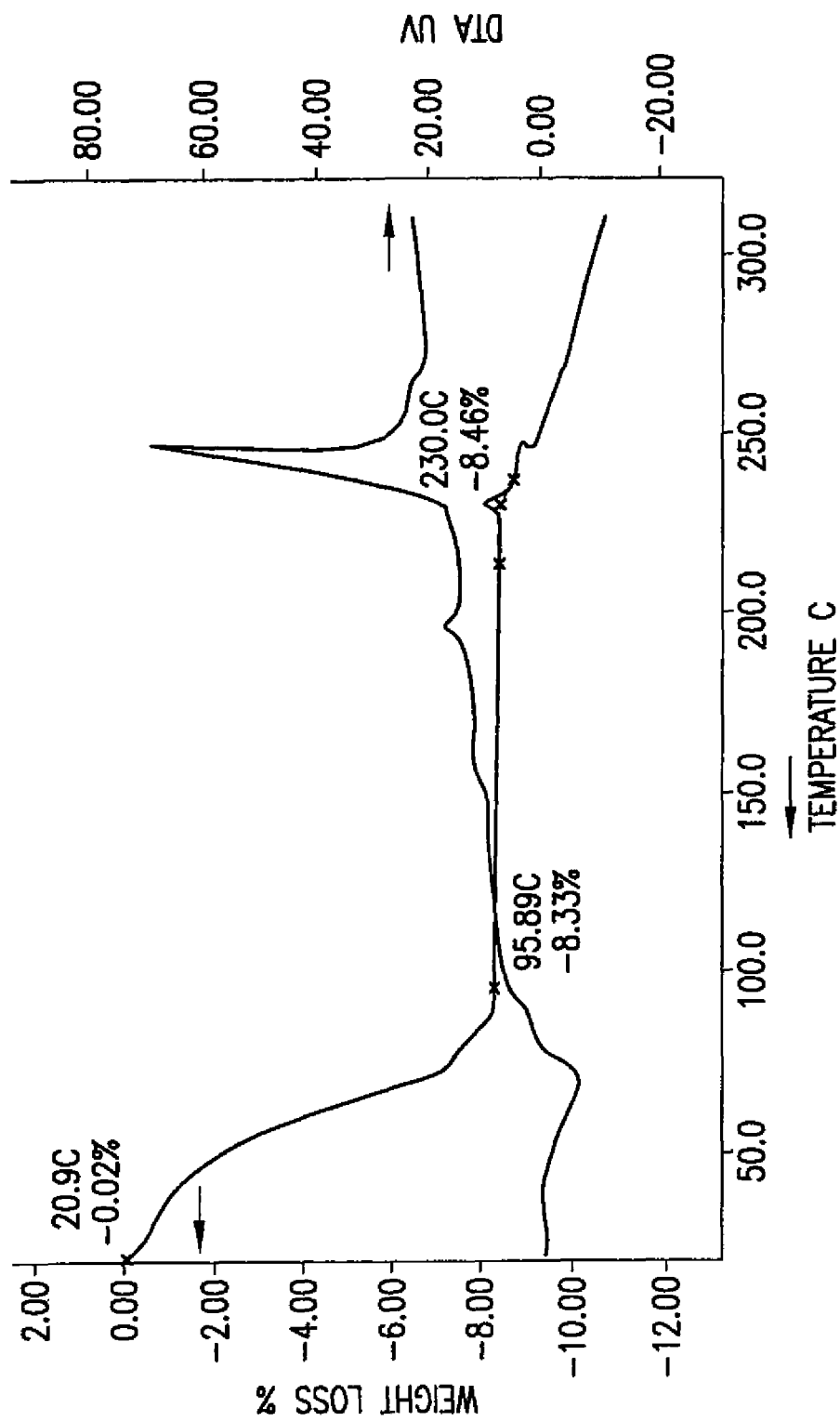
FIG. 1: presents a Thermogravimetric (TGA) thermogram (upper curve) and Differential Thermal Analysis (DTA) scan (lower curve) of product obtained upon suspending Form I (anhydrous compound IX in water) measured at 10° C./min under nitrogen. That product is Form V.

The present invention is directed to alternative forms of the title phosphodiesterase 4 inhibitor which has the structural formula shown immediately below:

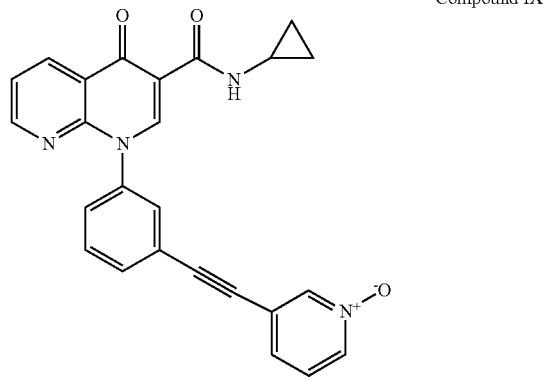

Compound IX

Preparation of Starting Material

As disclosed in Example 16 at page 53 of WO 03/018579, compound IX may be prepared by the method shown below. WO 03/018579 is hereby incorporated by reference.

Preparative Example 1

N-Isopropyl-1-[3-(phenylethynyl)phenyl]-1,4-dihydro[1,8]naphthyridin-4-one-3-carboxamide Step 1: Ethyl 3-(3-bromoanilino)-2-(2-chloronicotinoyl) acrylate A mixture of ethyl 2-chloronicotinoyl acetate (41.1 g, 180.5 mmol), triethyl orthoformate (40.12 g, 271 mmol) and acetic anhydride (92.05 g, 902.5 mmol) was heated at 130° C. for 2.5 hours. The volatile components were distilled off and the resulting residue was co-evaporated twice with xylene. The oily residue was dissolved in methylene chloride (250 mL) and 3-bromoaniline (37.25 g, 216.6 mmol) was added slowly. The resulting solution was stirred at room temperature for 18 hours, and the solvent evaporated away. The resulting crude compound was used as such in the next step.

Step 2: Ethyl 1-(3-bromophenyl)-1,4-dihydro[1,8]naphthyridin-4-one-3-carboxylate The crude compound from Step 1 was dissolved in tetrahydrofuran (500 mL), the solution was cooled to 0° C., and sodium hydride (as a 60% dispersion in oil, 9.4 g, 235 mmol) was added in portions. After stirring at 0° for 1 hour, the resulting mixture was allowed to warm up to room temperature. After 2 hours, water (400 mL) was added to the resulting suspension and the insoluble solid was filtered and washed copiously with water. When dry, the solid was stirred in ether (150 mL) at room temperature for 24 hours and filtered to afford the ethyl 1-(3-bromophenyl)-1,4-dihydro[1,8]naphthyridin-4-one-3-carboxylate compound as a cream-colored solid.

$^1$H NMR (Acetone-$d_6$) δ 1.32 (t, 3H), 4.29 (q, 2H), 7.54-7.63 (m, 2H), 7.69 (dd, 1H), 7.78 (dd, 1H), 7.93 (s, 1H), 8.66-8.71 (m, 3H).

Step 3: 1-(3-Bromophen)-1,4-dihydro[1,8]naphthyridin-4-one-3-carboxylic acid

A suspension of ethyl 1-(3-bromophenyl)-1,4-dihydro[1,8]naphthyridin-4-one-3-carboxylate from Step 2 (52.5 g, 140.7 mmol) in a mixture of tetrahydrofuran (400 mL), methanol (400 mL) and 1N aqueous sodium hydroxide (280 mL) was heated at ca 50° C. with stirring for 20 minutes. After cooling, the mixture was diluted with water (300 mL) and 1N aqueous HCl (325 mL) was added. After stirring for 45 minutes, the precipitate was filtered, washed well with water and dried to afford the 1-(3-bromophenyl)-1,4-dihydro[1,8]naphthyridin-4-one-3-carboxylic acid as a cream-colored solid.

$^1$H NMR (Acetone-$d_6$) δ 7.65 (t, 1H), 7.76 (m, 2H), 7.84 (d, 1H), 7.99 (s, 1), 8.87 (m, 2H), 9.01 (s, 1H).

Step 4: N-Isopropyl-1-(3-bromophenyl)-1,4-dihydro[1,8]naphthyridin-4-one-3-carboxamide To a suspension of 1-(3-bromophenyl)-1,4-dihydro[1,8]naphthyridin-4-one-3-carboxylic acid from Step 3 (26.3 g, 76 mmol) and triethylamine (23.2 g, 230 mmol) in tetrahydrofuran (1000 mL) at 0° C. was added isobutyl chloroformate (18.85 g, 138 mmol). After stirring at 0° C. for 2 hours, isopropylamine (23 g, 390 mmol) was added and the mixture was allowed to warm up to room temperature and stirred overnight. The mixture was then partitioned between ethyl acetate and water, the organic phase was dried and evaporated to a solid which was stirred in ether at room temperature for 3 hours and filtered to afford the N-isopropyl-1-(3-bromophenyl)-1,4-dihydro[1,8]naphthyridin-4-one-3-carboxamide as a white solid.

$^1$H NMR (Acetone-$d_6$) δ 1.25 (d, 6H), 4.17 (m, 1H), 7.59-7.63 (m, 2H), 7.70 (d, 1), 7.80 (d, 1H), 7.94 (s, 1H), 8.73 (m, 1H), 8.78 (d, 1H), 8.85 (s, 1H), 9.61 (br, NH).

Step 5: N-Isopropyl-1-[(3-phenylethynyl)phenyl]-1, 4-dihydro[1,8]naphthyridin-4-one-3-carboxamide A mixture of amide from Step 4, phenylacetylene (1.9 eq), triethylamine (1.6 eq), triphenylphosphine (0.06 eq) and bis(triphenylphosphine)palladium (H) chloride (0.05 eq) in THF (16 mL/mmol) was stirred at room temperature for 20 minutes. Copper (I) iodide (5 mg/mmol) was added and the mixture was stirred at reflux for 18 hours. After cooling, the mixture was quenched with saturated aqueous ammonium chloride solution and partitioned between ethyl acetate and water. The organic phase was dried over magnesium sulfate and the crude product was chromatographed on silica gel eluting with a 1:9 mixture of ether and methylene chloride to afford a solid which was stirred in ether at room temperature and filtered to yield the N-Isopropyl-1-[(3-phenylethynyl)phenyl]-1,4-dihydro[1,8]naphthyridin-4-one-3-carboxamide compound as a solid.

$^1$H NMR (Acetone-$d_6$) δ 1.24 (d, 6H), 4.18 (m, 1H), 7.42 (m, 3H), 7.56-7.61 (m, 3H), 7.69 (m, 2H), 7.76 (m, 1H), 7.85 (s, 1H), 8.73 (m, 1H), 8.77 (dd, 1H), 8.88 (s, 1H), 9.62 (br, NH).

Preparative Example 2

N-Isopropyl-1-(3-ethynylphenyl)-1,4-dihydro[1,8] naphthyridin-4-one-3-carboxamide Step 1: N-Isopropyl-1-[3-(trimethylsilylethynyl)phenyl]-1,4-dihydro[1,8]naphthyridin-4-one-3-carboxamide Following the procedure of Step 5 of PREPARATIVE EXAMPLE 1, but substituting trimethylsilylacetylene for phenylacetylene, the N-isopropyl-1-[3-(trimethylsilylethynyl)phenyl]-1,4-dihydro[1,8]naphthyridin-4-one-3-carboxamide product was obtained and used in the next step without further purification.

Step 2: N-Isopropyl-1-(3-ethynylphenyl)-1,4-dihydro [1,8]naphthyridin-4-one-3-carboxamide The crude product from Step 1 was dissolved in methanol (12 mL/mmol) and 1N aqueous sodium hydroxide was added (3 eq), resulting in a suspension. The suspension mixture was stirred at room temperature for 2 hours and the methanol was evaporated. The resulting aqueous suspension was diluted with water and the product was extracted out with ethyl acetate. The crude product was chromatographed on silica gel eluting with 10% ether in methylene chloride to afford the N-isopropyl-1-(3-ethynylphenyl)-1,4-dihydro[1,8]naphthyridin-4-one-3-carboxamide compound as a solid.

$^1$H NMR (Acetone-$d_6$) δ 1.24 (d, 61-1), 3.81 (s, 1H), 4.17 (m, 1H), 7.59 (m, 1H), 7.64-7.71 (m, 3H), 7.81 (s, 1H), 8.72 (m, 1H), 8.76 (dd, 1H), 8.84 (s, 1H), 9.61 (br, NH).

Preparative Example 3

N-Cyclopropyl-1-(3-ethynylphenyl)-1,4-dihydro[1,8] naphthyridin-4-one-3-carboxamide Step 1: N-Cyclopropyl-1-(3-bromophenyl)-1,4-dihydro[1,8]naphthyridin-4-one-3-carboxamide Following the procedure of Step 4 of PREPARATIVE EXAMPLE 1, but substituting cyclopropylamine for isopropylamine, the N-cyclopropyl-1-(3-bromophenyl)-1,4-dihydro[1,8]naphthyridin-4-one-3-carboxamide was obtained as a fluffy white solid.

$^1$H NMR (Acetone-$d_6$) δ 0.59 (m, 2H), 0.80 (m, 2H), 2.96 (m, 1H), 7.59-7.68 (m, 2H), 7.72 (dd, 1H), 7.82 (dd, 1H), 7.97 (s, 1H), 8.72-8.81 (m, 2H), 8.89 (s, 1H), 9.70 (br, NH).

Steps 2 and 3: N-Cyclopropyl-1-(3-ethynylphenyl)-1,4-dihydro[1,8]naphthyridin-4-one-3-carboxamide Following the procedures of Steps 1 and 2 of PREPARATIVE EXAMPLE 2, but substituting the product from step 1 for N-isopropyl-1-(3-bromophenyl)-1,4-dihydro[1,8]naphthyridin-4-one-3-carboxamide, the N-Cyclopropyl-1-(3-ethynylphenyl)-1,4-dihydro[1,8]naphthyridin-4-one-3-carboxamide compound was obtained as a solid.

$^1$H NMR (CDCl$_3$) δ 0.66 (m, 2H), 0.85 (m, 2H), 2.97 (m, 1H), 3.18 (s, 1H), 7.42 (d, 1H), 7.47 (m, 1H), 7.52-7.58 (m, 2H), 7.65 (d, 1H), 8.70 (m, 1H), 8.80 (dd, 1H), 8.98 (s, 1H), 9.74 (br, NH).

Preparative Example 4

N-Isopropyl-1-[3-(3-hydroxy-3-phenylbut-1-ynyl) phenyl]-1,4-dihydro[1,8]naphthyridin-4-one-3-carboxamide A mixture of N-isopropyl-1-(3-bromophenyl)-1,4-dihydro [1,8]naphthyridin-4-one-3-carboxamide from Step 4 of PREPARATIVE EXAMPLE 1, 2-phenyl-3-butyn-2-ol (2 eq), triethylamine (1.66 eq), bis(diphenylphosphino)ferrocene]dichloropalladium(II) (0.05 eq), and copper (I) iodide (5 mg/mmol) in DMF (20 mL/mmol) was heated at 85° C. for 18 hours. After cooling to room temperature, the resulting mixture was quenched with saturated aqueous ammonium chloride solution and partitioned between ethyl acetate and water. The crude product from the organic phase was chromatographed on silica gel eluting with 20% ether in methylene chloride. The purified product was stirred in ether at room temperature for 3 hours and filtered to afford the title compound as a white solid.

$^1$H NMR (Acetone-$d_6$) δ 1.24 (d, 6H), 1.79 (s, 3H), 4.18 (m, 1H), 5.22 (s, 1H, OH), 7.26 (t, 1H), 7.35 (t, 2H), 7.59 (m, 1H), 7.66 (m, 3H), 7.73 (d, 2H), 7.76 (s, 1H), 8.72 (m, 1H), 8.77 (dd, 1H), 8.84 (s, 1H), 9.62 (br, NH).

PDE 4 Inhibitor Compound IX

N-Cyclopropyl-1-[3-(1-oxido-3-pyridinylethynyl)phenyl]-1,4-dihydro[1,8]naphthyridin-4-one-3-carboxamide

Step 1: 3-Ethynylpyridine N-oxide

To a solution of 3-ethynylpyridine in methylene chloride (5 mL/mmol) at room temperature was added m-chloroperoxybenzoic acid (m-CPBA, 70% purity, 1.2 eq) and the resulting mixture was stirred for 2 hours. A further amount of m-CPBA was added (0.25 eq) and stirring was continued for 1 hour. Calcium hydroxide was added (2 eq) and after 15 minutes the mixture was filtered through celite and the filtrate was evaporated. The solid residue was stirred in ether for 3 hours and filtered to afford the 3-ethynylpyridine N-oxide compound as a white solid.

Step 2: N-Cyclopropyl-1-[3-(1-oxido-3-pyridinylethynyl)phenyl]-1,4-dihydro[1,8]naphthyridin-4-one-3-carboxamide Following the procedure of PREPARATIVE EXAMPLE 4, but substituting N-cyclopropyl-1-(3-bromophenyl)-1,4-dihydro[1,8]naphthyridin-4-one-3-carboxamide from Step 1 of PREPARATIVE EXAMPLE 3 for N-isopropyl-1-(3-bromophenyl)-1,4-dihydro[1,8]naphthyridin-4-one-3-carboxamide, and 3-ethynylpyridine N-oxide from Step 1 for 2-phenyl-3-butyn-2-ol, the N-cyclopropyl-1-[3-(1-oxido-3-pyridinylethynyl)phenyl]-1,4-dihydro[1,8]naphthyridin-4-one-3-carboxamide compound was obtained as a white solid.

$^1$H NMR (CDCl$_3$) δ 0.66 (m, 2H), 0.84 (m, 2H), 2.96 (m, 1H), 7.26 (m, 1H), 7.37 (d, 1H), 7.45-7.48 (m, 2H), 7.58-7.62 (m, 2H), 7.69 (d, 1H), 8.16 (d, 1H), 8.31 (s, 1H), 8.69 (m, 1H), 8.79 (dd, 1H), 8.99 (s, 1H), 9.73 (br, NH).

Alternative Procedure of Making PDE 4 Inhibitor Compound IX

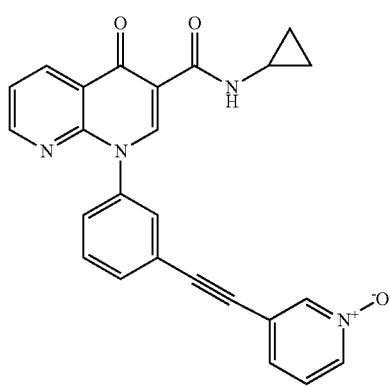

Compound IX

N-Cyclopropyl-1-{3-[(1-oxidopryidin-3-yl)ethynyl]phenyl}-4-oxo-1,4-dihydro-1,8-naphthyridine-3-carboxyamide (Compound IX)

Step 1:

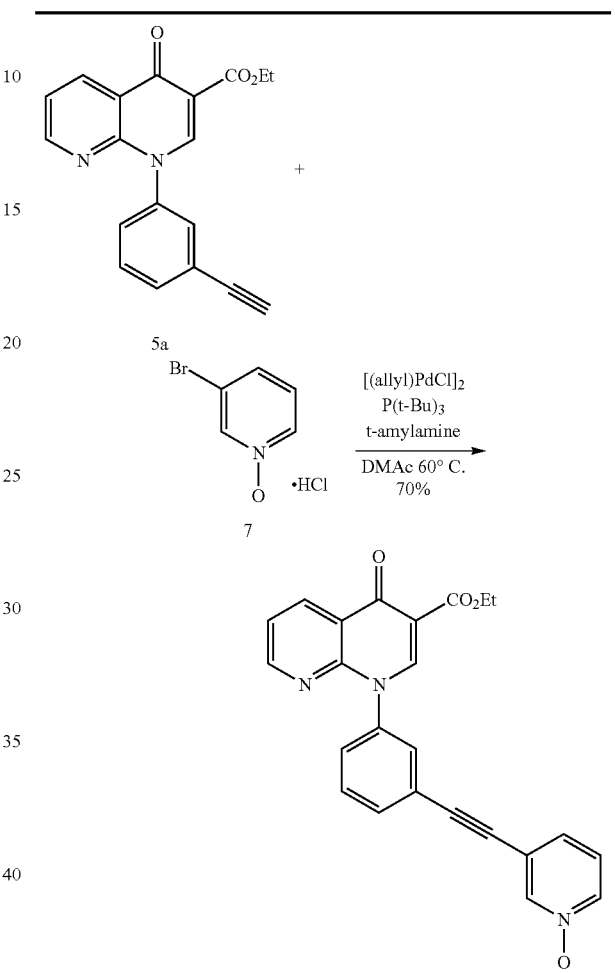

| Materials | MW | Amount | Moles | Eq |
|---|---|---|---|---|
| Ethyl ester naphthyridone-phenylacetylene | 318.33 | 2.50 Kg | 7.85 | 1.0 |
| 3-Bromopyridine-N-oxide HCl salt | 210.46 | 1.82 Kg | 8.64 | 1.1 |
| Tert-amylamine | 87.17 d = 0.746 | 2.7 L | 45.6 | 3.0 |
| Allylpalladiumchloride dimer | 365.85 | 72 g | 0.2 | 2.5 mol % |
| Tri-t-butylphosphine | 10% in hexanes (0.33M) | 2.38 L | 0.8 | 10 mol % |
| Dimethylaminoacetamide (DMAc) | solvent | 60 L | — | 24 vol |
| water | anti-solvent | 90 L | — | 36 vol |
| n-Butanol | rinse solvent | 87.6 L | — | 35 vol |

A 100 L round bottom flask was equipped with a reflux condenser and nitrogen sweep, and charged with bromopyridine-N-oxide HCl salt, followed by DMAc 12.5 L, and cooled with ice bath. Neat t-amylamine was added via dropping funnel over 1 hour. Addition of amine was noted to be mildly exothermic: temperature rose from 5° C. to 10° C. The phosphine solution was added to produce a light yellow, homogeneous solution. Next, the π-allylpalladium dimer was added as a slurry in DMAc 1.5 L. The reaction was allowed to stir at 10° C. for 30 minutes. The acetylene compound was weighed out into a carboy and DMAc 9.9 Kg added. This acetylene solution was added into the reaction flask. The carboy was rinsed with DMAc 22 Kg and added to the reaction mixture. Enough DMAc was added to achieve a total of 60 L. This milky yellow solution was heated to 60° C., becoming a homogeneous brown solution, until reaction was complete, judged by consumption of the acetylene compound. The reaction was cooled to 0° C. before adding water 90 L to precipitate product from solution. The slurry was filtered to collect product. To remove palladium, the cake was washed with 87.5 L of n-butanol on the filter pot, and then dried in vacuum oven at 50° C. under nitrogen stream overnight to give white solids 2.68 Kg, 83% yield.

NMR $^1$H (CDCl$_3$ 400 MHz) δ: 1.35 (t, J=7.1 Hz, 3H), 4.34 (q, J=7.1, 2H), 7.28 (dd, J=8.0, 6.8 Hz, 1H), 7.34 (dT, J=8.0, 1.2 Hz, 1H), 7.38 (dd, J=8.0, 4.4 Hz, 1H), 7.49 (ddd, J=8.0, 2.4, 1.2 Hz, 1H), 7.58 (t, J=7.9 Hz, 1H), 7.64 (t, J=1.8 Hz, 1H), 7.67 (dt, J=7.6, 1.2 Hz, 1H), 8.12 (dt, J=6.5, 1.1 Hz, 1H), 8.27 (s, 1H), 8.59 (dd, J=4.4, 1.9 Hz, 1H), 8.64 (s, 1H), 8.74 (dd, J=8.0, 1.9 Hz, 1H).

NMR $^{13}$C (CDCl$_3$ 400 MHz) δ: 14.3, 61.1, 84.7, 92.4, 112.8, 121.4, 122.7, 123.0, 123.2, 125.8, 128.3, 128.5, 129.8, 130.7, 132.5, 136.8, 139.1, 141.0, 149.0, 149.9, 152.5, 164.6, 174.5.

An alternative method of Palladium reduction has also been used and is as follows:

| Materials | MW | Amount | Moles | Eq |
|---|---|---|---|---|
| Ester product | 411.14 | 0.718 Kg | 7.85 | 1.0 |
| Darco G-60 | — | 0.359 Kg | — | 50 wt % |
| Methanol | solvent | 82 L | — | 50 vols |

After precipitation with water, the wet filter cake was dried under a nitrogen stream. A 100 L round bottom flask was equipped with a reflux condenser, stir paddle, and nitrogen sweep, then charged with the ester product and methanol 72 L. Mixture was heated to 60° C. until solids dissolved. Mixture was cooled to 55° C. and Darco G-60 was added as a slurry in 6 L methanol. Mixture was heated back to 60° C. for four hours. The solution was filtered through Solka Floc while warm to remove Darco. Solka Floc pad was rinsed with another 4 L of methanol. Combined filtrates were concentrated to 25 L volume, at which point a copious white precipitate was noted. This slurry can be carried forward into the amide formation step directly.

Step 2:

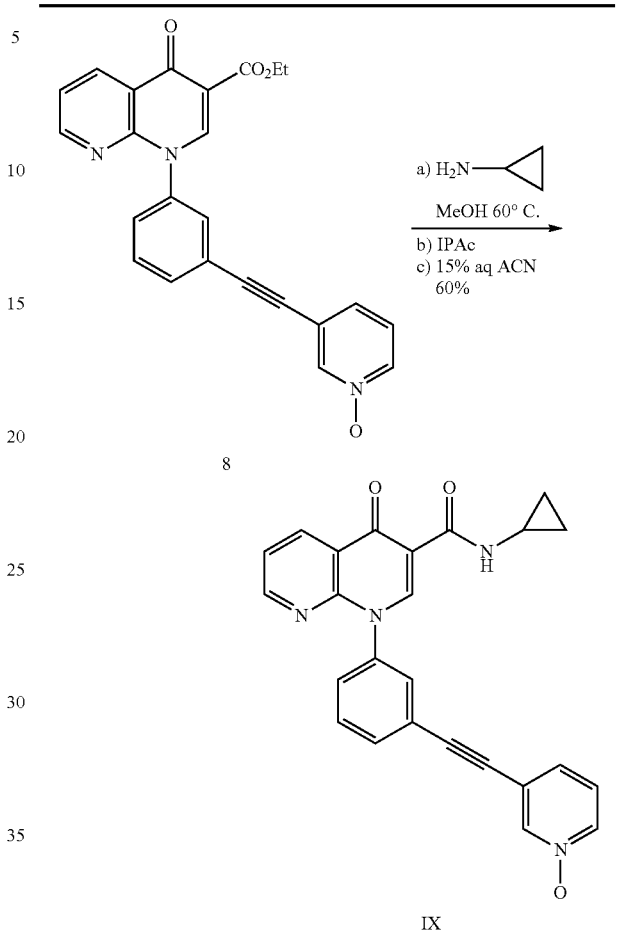

| Materials | MW | Amount | Moles | Eq |
|---|---|---|---|---|
| Penultimate ester | 411.41 | 1.4 Kg | 3.4 | 1.0 |
| Cyclopropylamine | 57.10, d =0.824 | 21 L | — | 15 vols |
| (Butylphosphite | 250, d = 0.915 | 46 mL | 0.17 | 5 mol %)* |
| Methanol | solvent | 21 L | — | 15 vols |
| Isopropyl acetate | anti-solvent | 72 L | — | — |
| 15% aq. acetonitrile | solvent | 24 L | — | 24 vols |
| In-line filter, 1 micron | | | | |

*Note that the parentheses around the butylphosphite data indicate that the experiment was run both with and without the butylphosphite.

A 100 L round bottom flask was equipped with a reflux condenser and nitrogen sweep, and charged with penultimate ester and methanol followed by cyclopropylamine. As indicated above, catalyst or Lewis acid can be added. The reaction was heated to 60° C. until consumption of the ester. The reaction was judged to be complete when esters were less than 2% by HPLC. Upon completion, the reaction was allowed to cool to 40° C. and concentrated to ~half volume. Isopropyl acetate was added while distilling out the remainder of the methanol and amine. After completion of the solvent switch to isopropyl acetate, the final volume was 20 L. The slurry was sampled and filtered. The cake was washed with 2 L of isopropyl acetate and then dried in vacuum oven at 50° C. under nitrogen stream overnight.

A 72 L round bottom flask was equipped with a reflux condenser and nitrogen sweep, and charged with Compound IX product solids and 24 L 15% aq. acetonitrile. The Slurry was heated to 60° C. All solids went into solution. Batch solution was filtered through a 1 micron in-line filter while warm into a second 72 L round bottom flask, then allowed to cool to 22° C. The slurry was filtered and solids dried in vacuum oven at 50° C. under nitrogen stream overnight to give 0.86 Kg of crystallized Compound IX, 60% yield.

NMR $^1$H (CDCl$_3$ 400 MHz) δ: 0.61-0.73 (m, 2H), 0.79-0.92 (m, 2H), 2.95-3.01 (m, 1H), 7.28 (dd, J=8.0, 6.8 Hz, 1H), 7.40 (d, J=8.0 Hz, 1H), 7.48 (dt, J=8.0, 4.4 Hz, 1H), 7.49 (ddd, J=8.0, 2.0, 1.2 Hz, 1H), 7.61 (t, J=8.0 Hz, 1H), 7.64 (m, J=2.0 Hz, 1H), 7.71 (dt, J7.6, 1.2 Hz, 1H), 8.19 (d, J=6.6 Hz, 1H), 8.34 (s, 1H), 8.70 (dd, J=4.6, 1.8 Hz, 1H), 8.80 (dd, J=8.0, 1.9 Hz, 1H), 9.00 (s, 1H), 9.74 (br d, J=3.6 Hz, 1H).

NMR $^{13}$C (CDCl$_3$ 400 MHz) δ: 6.5, 22.4, 84.6, 92.5, 113.5, 121.4, 122.0, 122.9, 123.2, 125.7, 128.4, 128.6, 129.8, 130.7, 132.6, 136.4, 139.0, 140.4, 141.1, 148.0, 149.7, 153.0, 165.1, 177.1.

Alternative Procedure Illustrating Amide Formation with Magnesium Chloride

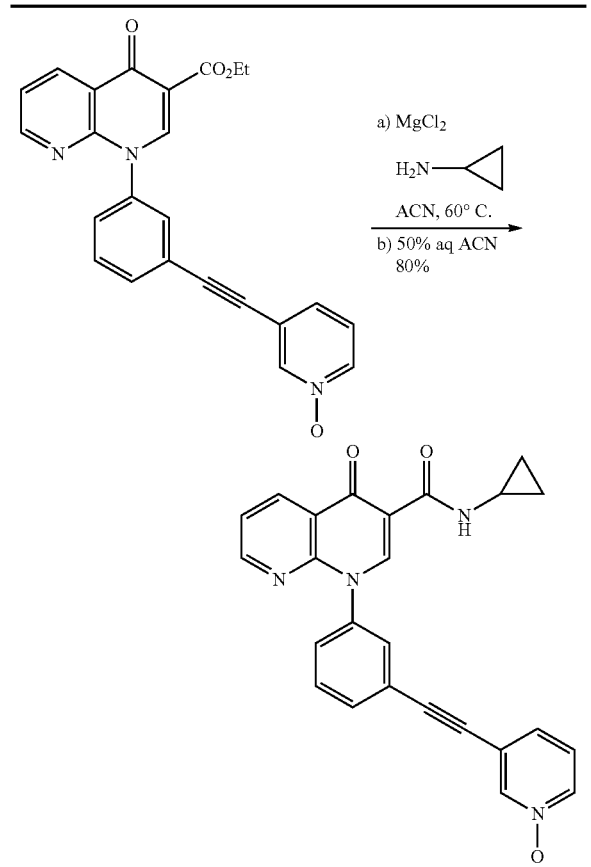

| Materials | MW | Amount | Moles | Eq |
|---|---|---|---|---|
| Penultimate ester | 411.41 | 1.0 Kg | 2.43 | 1.0 |
| Magnesium chloride | 95.22 | 0.231 Kg | 2.43 | 1.0 |
| Cyclopropylamine | 57.10, d = 0.824 | 10 L | — | 10 vol |
| Acetonitrile | solvent | 30 L | — | 30 vol |
|  |  | 16 L |  | 16 vol |
| Water | solvent | 8 L | — | 8 vol |
| sodium citrate | 294.10 | 0.79 Kg | 2.67 | 1.1 |
| In-line filter, 1 micron |  |  |  |  |

Process Description

A 72 L round bottom flask was equipped with a reflux condenser and nitrogen sweep, and charged with penultimate ester and acetonitrile followed by magnesium chloride and then cyclopropylamine. Reaction was heated to 60° C. until complete consumption of ester. Reaction was judged complete when esters were less than 0.5% by HPLC. Upon completion, reaction was allowed to cool to 40° C. and concentrated to half volume. Acetonitrile was added while distilling out remainder of cyclopropylamine. After complete solvent switch to acetonitrile, final volume was 8 L. Water 8 L was added and slurry was heated to 60° C. All solids went into solution. Batch solution was filtered through a 1 micron in-line filter while warm into a 22 L round bottom flask, then allowed to cool to 22° C. Slurry was filtered and solids dried in vacuum oven at 50° C. under nitrogen stream overnight to give 0.82 Kg of Compound IX, 80% yield.

Step 3: Recrystallization of Compound IX

| Materials | MW | Amount | Moles | Eq |
|---|---|---|---|---|
| Compound IX | 422.45 | 0.86 Kg | 2.0 | 1.0 |
| Ethanol | solvent | 20 L | — | 4.3 vols |

A 72 L round bottom flask was equipped with a reflux condenser and nitrogen sweep, and charged with Compound IX and ethanol. Slurry was heated to 50° C. with stirring until recrystallization was complete. Recrystallization was judged to be complete when greater than 95% Form I by solid-state NMR and/or powder diffraction X-ray. The batch was allowed to cool to 22° C., then filtered to collect white solids which were dried in a vacuum oven at 50° C. under a nitrogen stream overnight to give 0.74 Kg of the desired form. The solids were co-milled through a size 12 mesh to provide fluffy white solids 0.719 Kg.

Primary Examples

The polymorphic, amorphic and hydrated forms, of the present invention may be prepared and characterized, using the Compound IX (Form I), prepared as described above.

Compound IX Dihydrate

| Formula: | C$_{25}$H$_{18}$N$_4$O$_3$•2H$_2$O |
|---|---|
| Molecular Weight: | 422.447 + 36 = 458.447 |
| Colour, Form, Appearance: | crystalline fine white powder |

Physical Properties

Thermal Properties

Form I is the Compound IX product obtained by following the procedure of Preparative Example 4. As shown in Table 2, below, Form I is an anhydrate.

The dihydrate of Form I was obtained by isolating the excess solids from an aqueous suspension of Form I. For purposes of this specification, this Dihydrate of Form I is identified as Form V.

Preparation of the Dihydrate Form (Form V) and other Forms from the Compound IX (Form I)

40.47 mg of Form I (compound IX) and 2.0 mL water was added into a 20 mL glass sample vial, resulting in a suspension. The suspension was stirred overnight at 25° C. in the absence of the light for followed by centrifuging at 14 krpms for 15 minutes. The supernatant was removed from the sample vial and the centrifugation step was repeated. The recovered excess solid was kept in the sample vial and dried under ambient conditions for 3 days. The product is Form V as defined by XRPD.

The dihydrate (Form V) can also be obtained by stirring the Form I in aqueous solutions of 0.1N HCl, 0.01N HCl, and 0.1N NaOH followed by the centrifugation and drying.

Thermogravimetric Analysis (TGA)

TGA scans were obtained under nitrogen (100 mL/min) using a Seiko robotic TGA (RTG-220) at 10 deg/min, calibrated with indium, tin and a standard 20 mg weight. A TGA thermogram of Form V is shown in FIG. 1. A weight loss of 8.3% between 21-96° C. was measured for the Form V, corresponding to 2 moles of water per mole of compound. These results are very different from those of Form I, in which minimal weight loss up to 150° C. (0.5%) was found by TGA. No significant changes in degradation onset temperature were observed for the Form V (the dihydrate of compound IX) relative to the Form I.

Differential Scanning Calorimetry (DSC)

Figure 2:
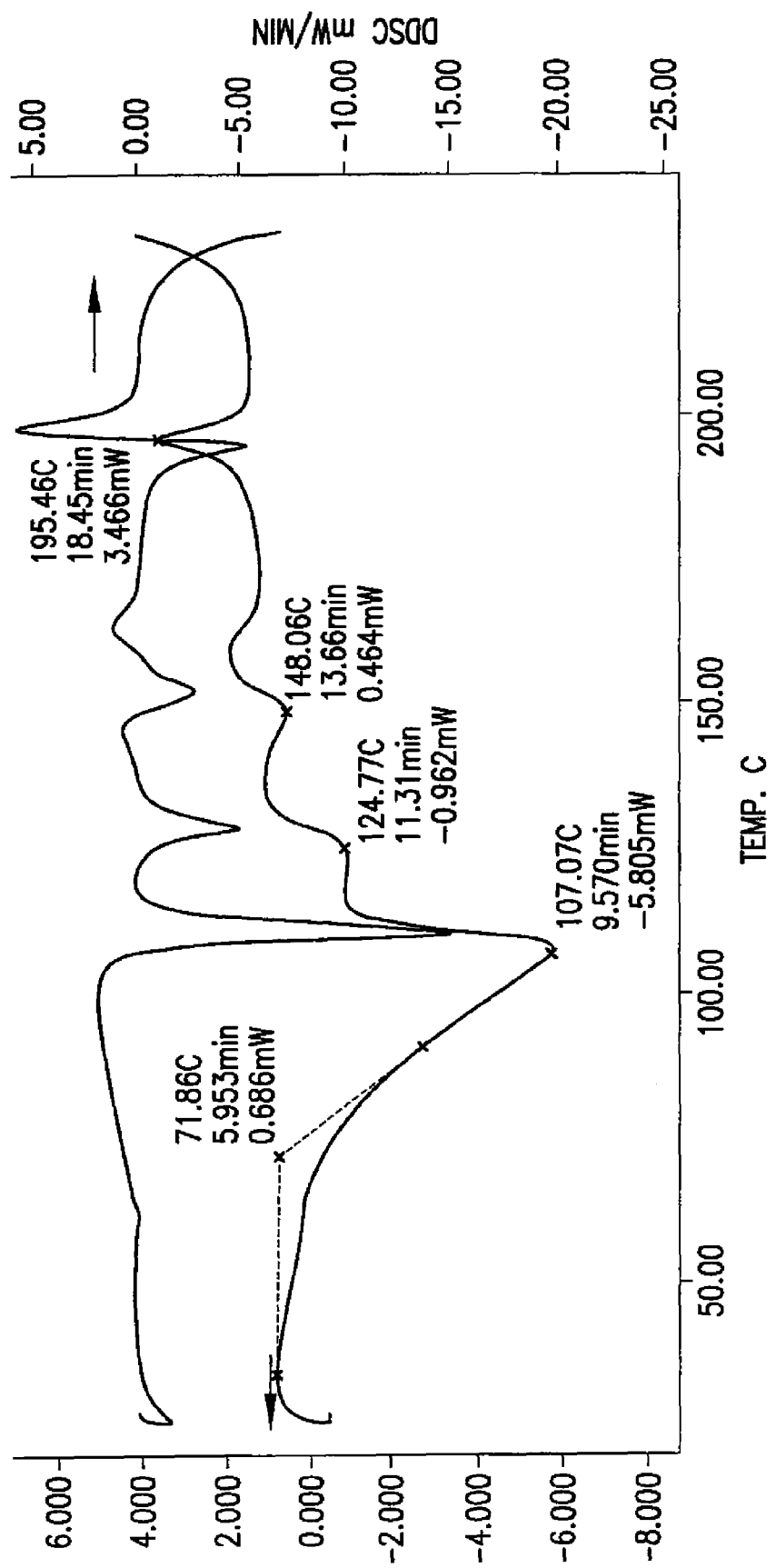
FIG. 2: presents a Differential Scanning calorimetry (DSC) scan of Form V measured in crimped aluminum pan at 10° C./min. The top curve is the derivative DSC (DDSC). Endothermic transitions are shown down.

The DSC thermal behaviour of the Form V in crimped aluminum pans under nitrogen (60 mL/min) was measured using a Seiko robotic DSC (RDC-220) at 10° C./min. The DSC was calibrated for temperature and heat flow with gallium, indium, and tin. The sample was heated from 20° C. to 240° C. and a typical DSC thermogram for Form V is shown in FIG. 2. Multiple endothermic transitions attributed to dehydration of the dihydrate (Form V) were observed before an exothermic transition peak at 195° C. These results are very different from the DSC studies of Form I where no transitions were observed prior to an exothermic transition at an onset temperature of 235.1±0.0° C.

Crystal Properties

X-Ray Powder Diffraction (XRPD)

XRPD patterns of Form V were measured using a Scintag XDS-2000, Si(Li) Peltier-cooled solid state detector at 45 kV and 40 mA, and divergent beam (2 mm and 4 mm) and receiving beam slits (0.5 mm and 0.2 mm) and 0.02°/step at 2 sec/step. The sample was measured on a quartz disk with spinning. Peak positions were verified using a certified Corundum plate (SRM 1976).

Figure 3:
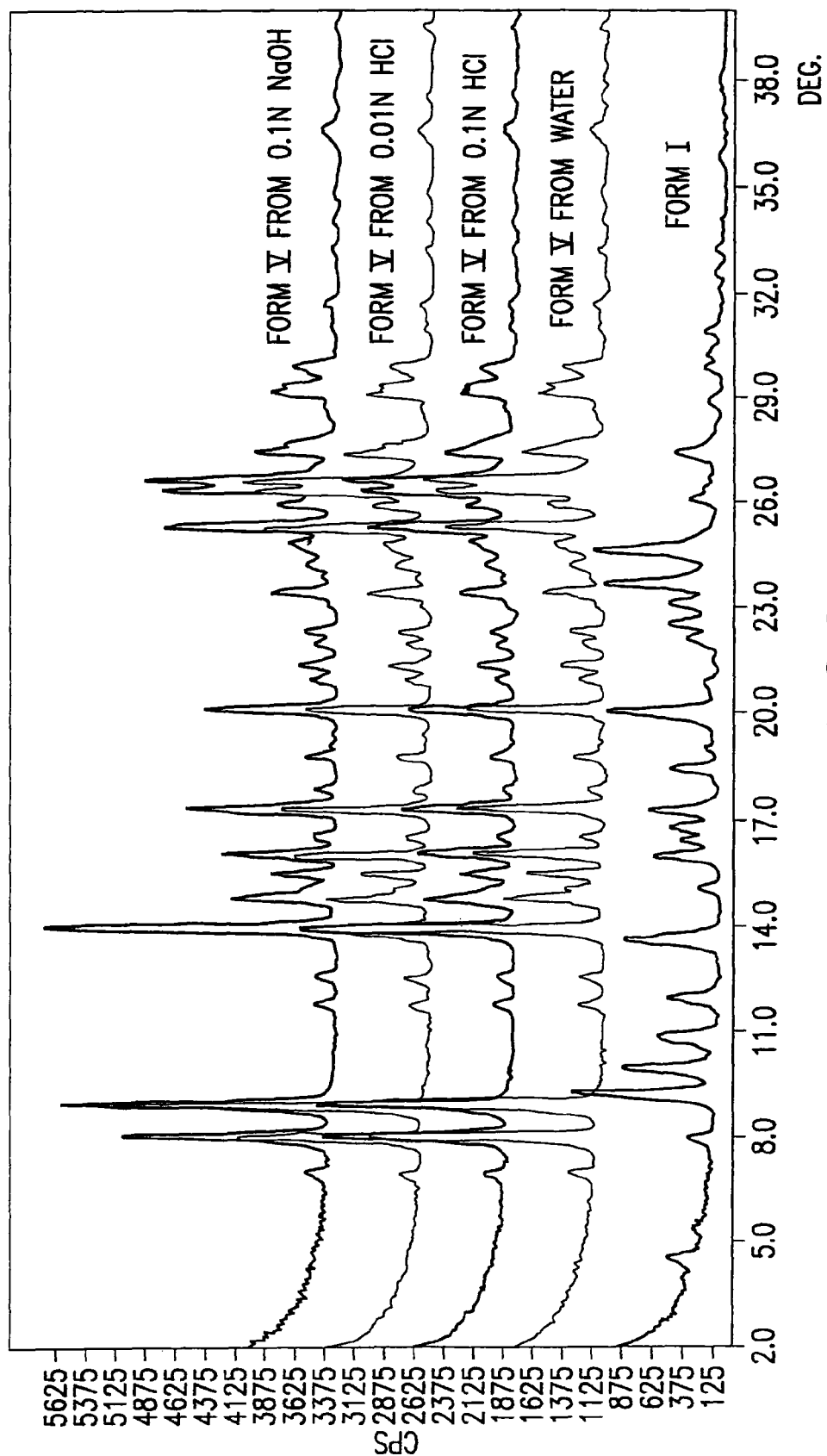
FIG. 3: presents the X-ray powder diffraction (XRPD) diffractograms of Form I (anhydrous Compound LX) and Form V (dihydrate of Form I) recovered from water, 0.1N HCl, 0.01N HCl, and 0.1N NaOH.

The crystal form (Form V) recovered from water, 0.01N HCl, 0.1N HCl, and 0.1N NaOH is different from Form I. Typical diffractograms of Form I and Form V are shown in FIG. 3.

Figure 4:
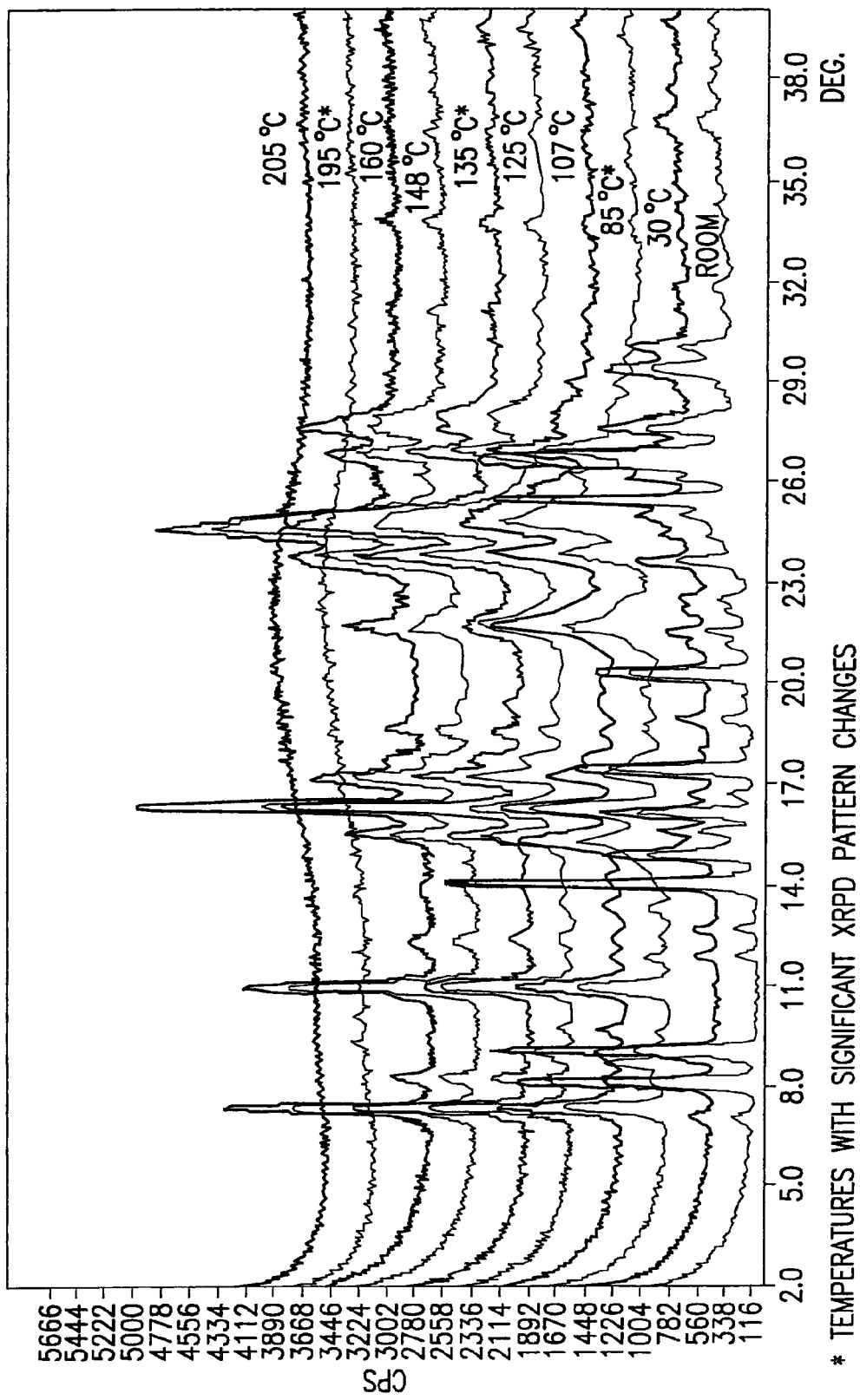
FIG. 4: presents the XRPD diffractograms of Form V at different temperatures.

Form V was also studied as a function of temperature using hot-stage XRPD and the diffraction patterns are shown in FIG. 4. Changes in some of the crystalline reflections were observed with increasing temperature, documenting the existence of different crystal forms at higher temperatures. A different diffraction pattern was observed at 85° C., showing that the dihydrate dehydrates at 85° C. A change in the crystalline pattern was observed between 125 and 135° C., corresponding to complete dehydration observed by TGA. A diffraction pattern change was also observed between 160 and 195° C., followed by melting.

The thermal stability of the Form V was evaluated by heating the sample for 24 h at 60° C. in air. The dihydrate (Form V) readily dehydrates within 10 min of heating losing approximately 8.5% by weight (corresponding to ca. 2 moles of water per mole base).

Hygroscopicity

Figure 5:
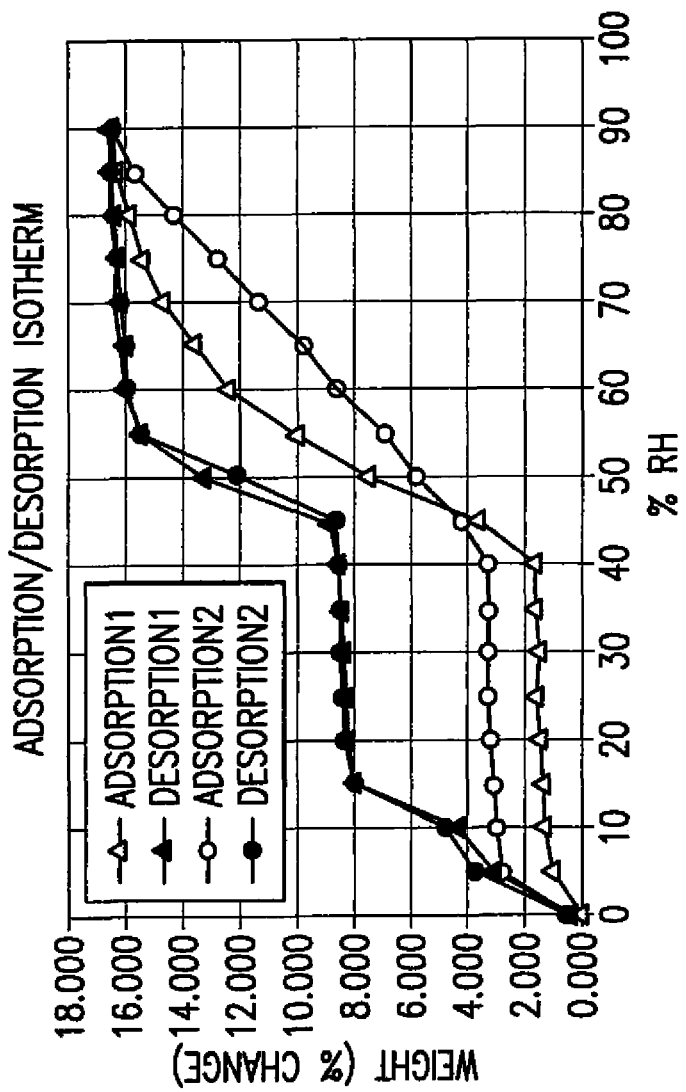
FIG. 5: presents two-round Moisture Adsorption/Desorption isotherms of Form V.
Figure 6:
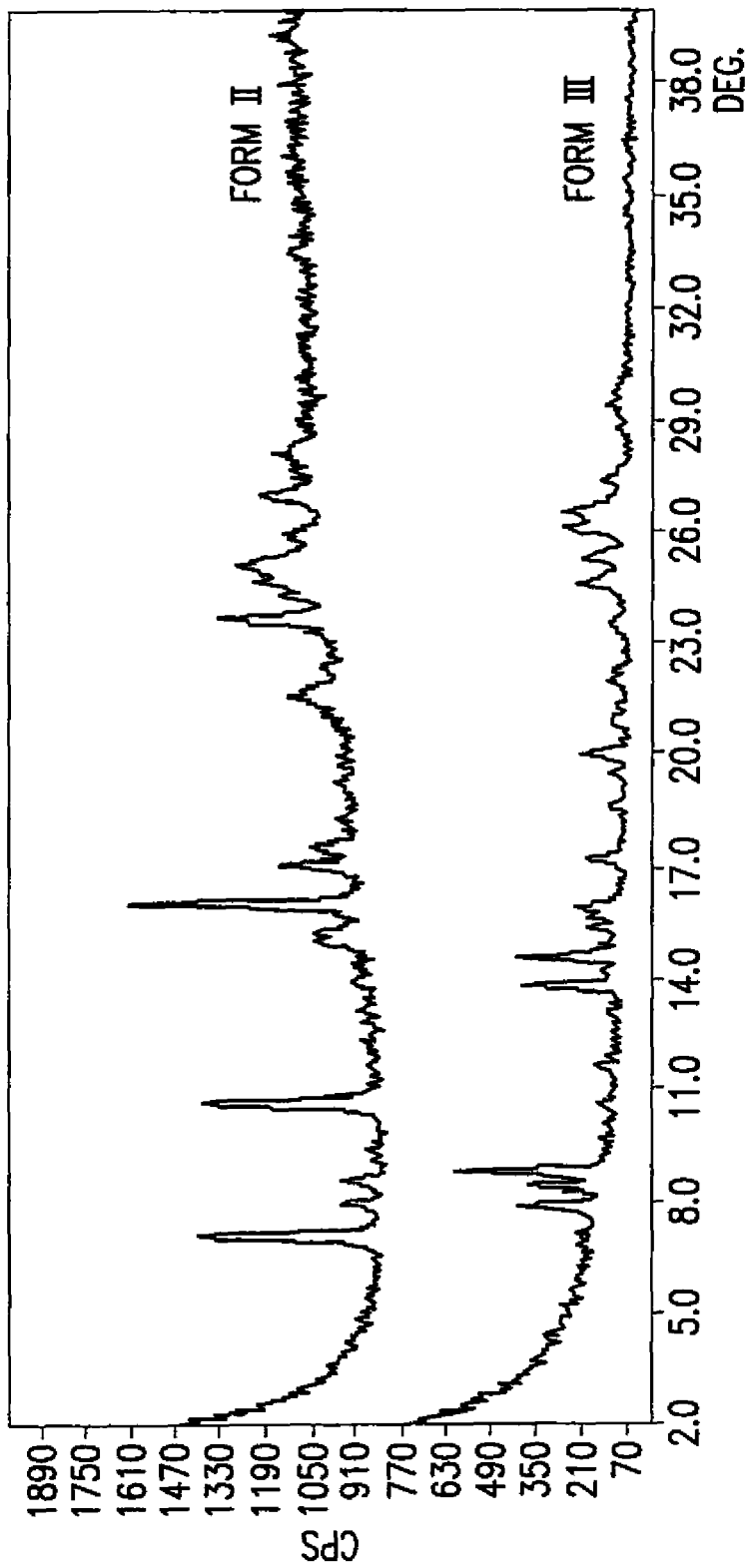
FIG. 6: presents the XRPD diffractograms of Form II by drying the Form V under vacuum and Form III obtained by drying the Form V at 60° C./air for 24 h.
Figure 7:
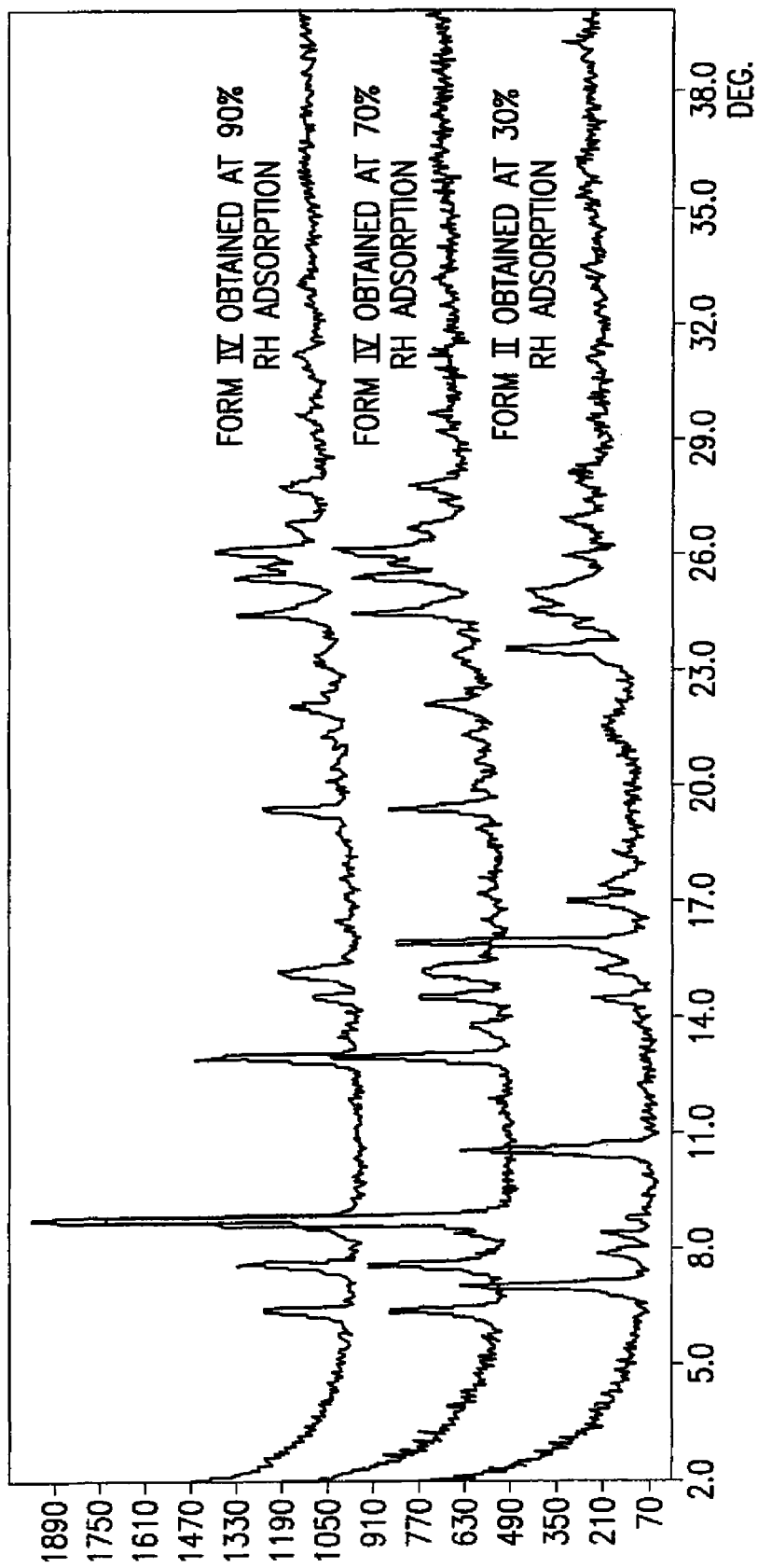
FIG. 7: presents XRPD diffratograms of products obtained upon subjecting Form V to different Relative Humidities (RH), upon adsorption. The products are Form II and Form N.

The moisture sorption isotherms of Form V was determined at 25° C. using a dynamic moisture balance (MB-300G) (VTI Corp., Hialeah, Fla.) calibrated for weight with 10 to 100 mg standard weights and for moisture with polyvinylpyrrolidone. The value for the weight equilibrium criterion for each relative humidity is calculated based on the weight of the sample and the drift in the balance (0.001 mg). A value of 8 min. was used for the time criteria. The moisture sorption profile of the dihydrate (Form V) (Adsorption 1/Desorption 1) after drying in vacuo for 2 h is shown in FIG. 5. Form V dehydrates on drying to a different crystal form as shown by vacuum X-ray powder diffraction in FIG. 6, losing approximately 8% by weight. For purposes of this specification, this dehydrated dihydrate is identified as Form H. This form appears to be the same as that obtained by heating the sample at 125° C., but different from that obtained on drying at 60° C. in air for 24 h. The latter form is identified as Form III. The Form II (dehydrated dihydrate) is hygroscopic converting to a hemihydrate between ca. 10-40% RH and a tetrahydrate at 90% RH (FIG. 5 and FIG. 7). However, the XRPD pattern for the hemihydrate is the same as that of the dehydrated dihydrate (Form II). For purposes of this specification this hemihydrate and tetrahydrate are identified as Form II and Form IV, respectively.

A second hemihydrate (Form VI) and an Anhydrous form (Form VII) of Compound IX have also been identified.

Procedure for Making Form VI—A Second Hemihydrate

A flask was charged with Compound IX Form I 1.1 Kg and a 15% aqueous ethanol solution, and heated to 70° C. with stirring. All solids dissolved. Heating was discontinued and batch allowed to cool to 18° C. overnight. Batch was poured onto filter and then dried in vacuum oven at 40° C. overnight to give 943 g of Form VI confirmed by XRPD.

Thermal Properties

Figure 12:
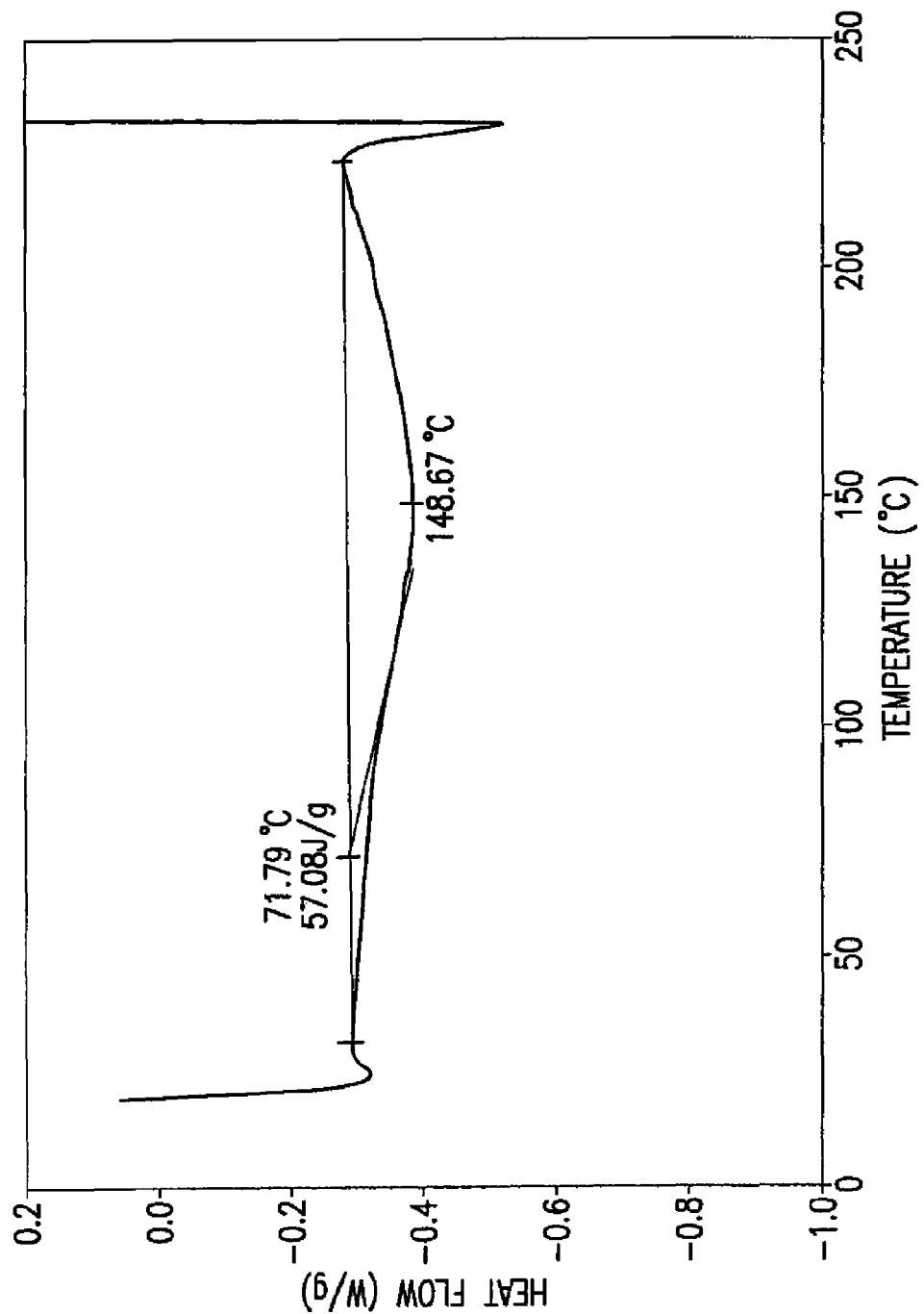
FIG. 12: presents a Differential Scanning calorimetry (DSC) scan of Form VI measured in crimped aluminum pan at 10° C./min.
Figure 13:
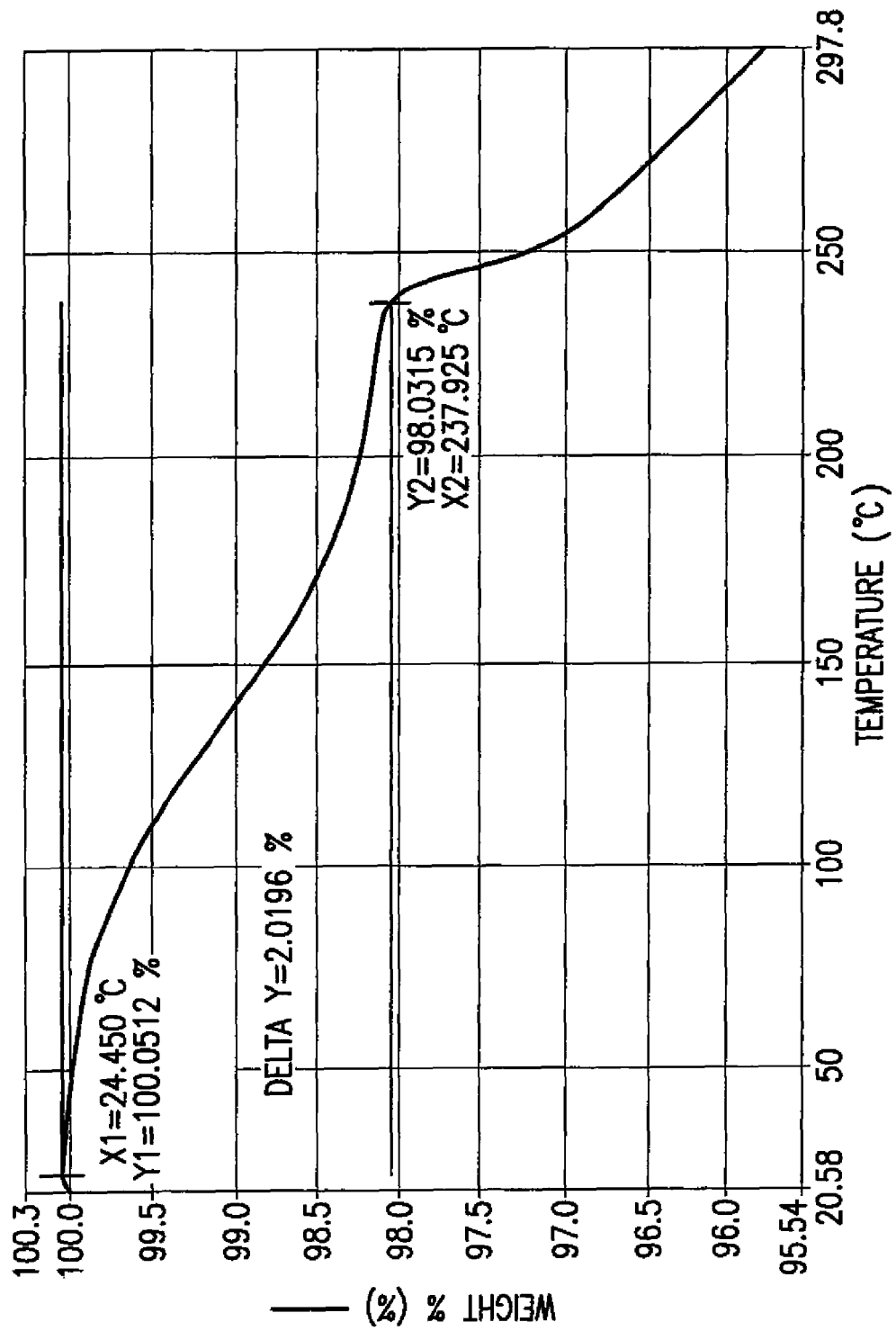
FIG. 13: presents a TGA thermogram of Form VI.

The DSC scan of Form VI is shown in FIG. 12. TA Instruments DSC 2910 was used. The instrument was calibrated with indium for temperature and heat flow. The heating rate was 10 C./min and the sample was heated to 300 C. under $N_2$ purge. A broad endotherm corresponding to water loss from the hemihydrate is observed with an onset at 72 C. prior to melting and degradation.

Thermogravimetric analysis was carried out using a Perkin Elmer TGA-7 system with N2 flow. The sample was heated from 20 C. to 300 C. at 10 C./min. The weight was calibrated with indium and a standard 20 mg weight. A TG curve for Form VI is shown is FIG. 11 A weight loss of 2.0% is observed corresponding to ½ mole of water per mole of compound.

XRPD Pattern

Figure 14:
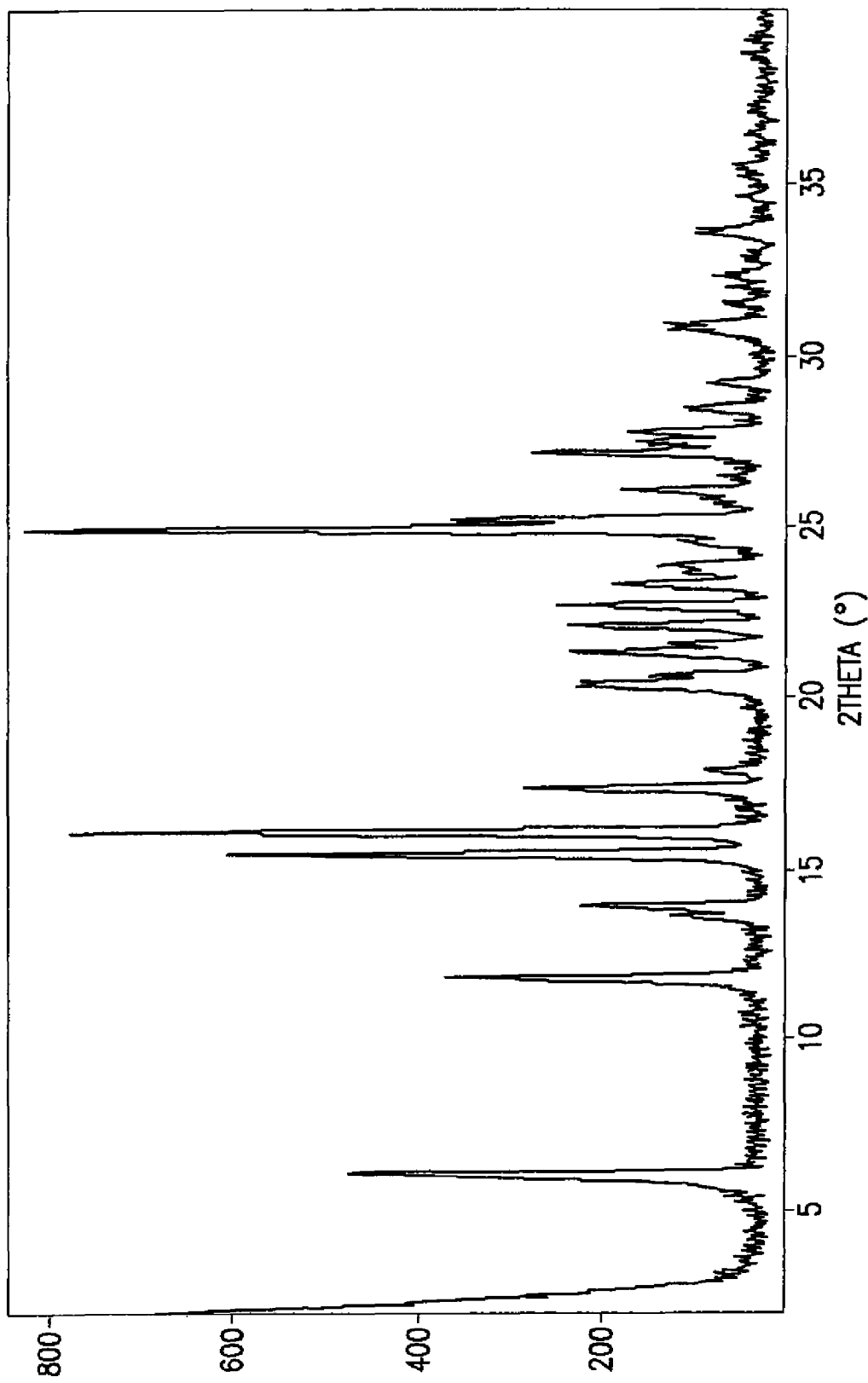
FIG. 14: presents XRPD diffractograms for Form VI.

XRPD pattern was obtained on a Philips XRG3100 instrument operating at 40 kV and 45 mA. A flat sample changer was used. The peak positions were calibrated with a Si reference sample. The XRPD pattern of Form VI is shown in FIG. 14 and is different from that of the Form II hemihydrate. The characteristic peaks corresponding to Form VI are 6.0, 15.3, 15.9, 23.8 and 25.0 degrees 2-theta.

Procedure for Making Form VII—Anhydrate Obtained on Drying Hemihydrate

About 50 mg of Form VI was dried in a vacuum oven ~60-80 C. The solids isolated after the drying gave an XRPD pattern that is slightly different from Form VI and is labeled Form VII.

Thermal Properties

Figure 15:
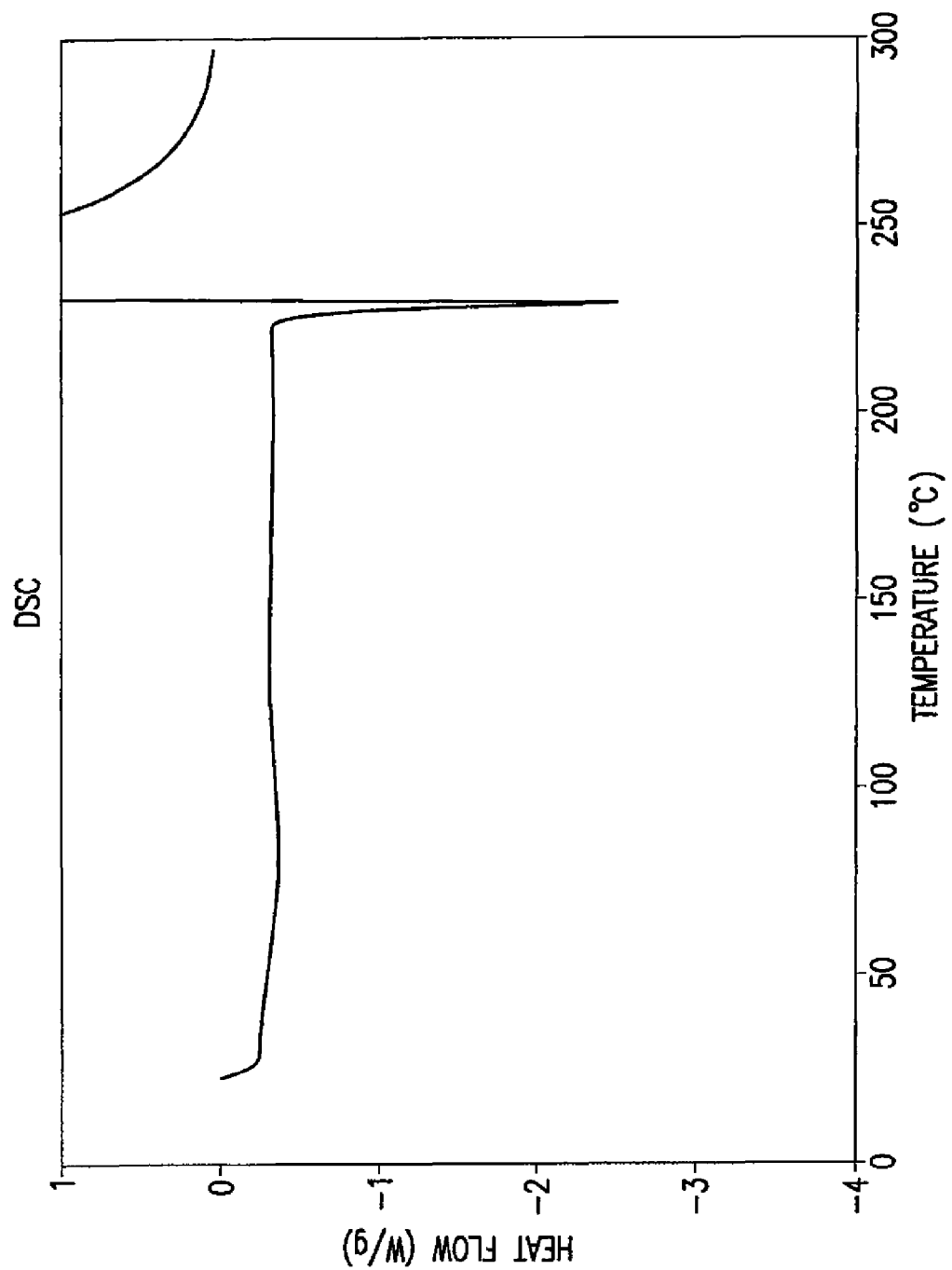
FIG. 15: presents a Differential Scanning calorimetry (DSC) scan of Form VII measured in crimped aluminum pan at 10° C./min.

The DSC scan of Form VII is shown in FIG. 15. TA Instruments DSC 2910 was used. The instrument was calibrated with indium for temperature and heat flow. The heating rate was 10 C./min and the sample was heated to 300 C. under $N_2$ purge. The onset of melting is 227 C.

Figure 16:
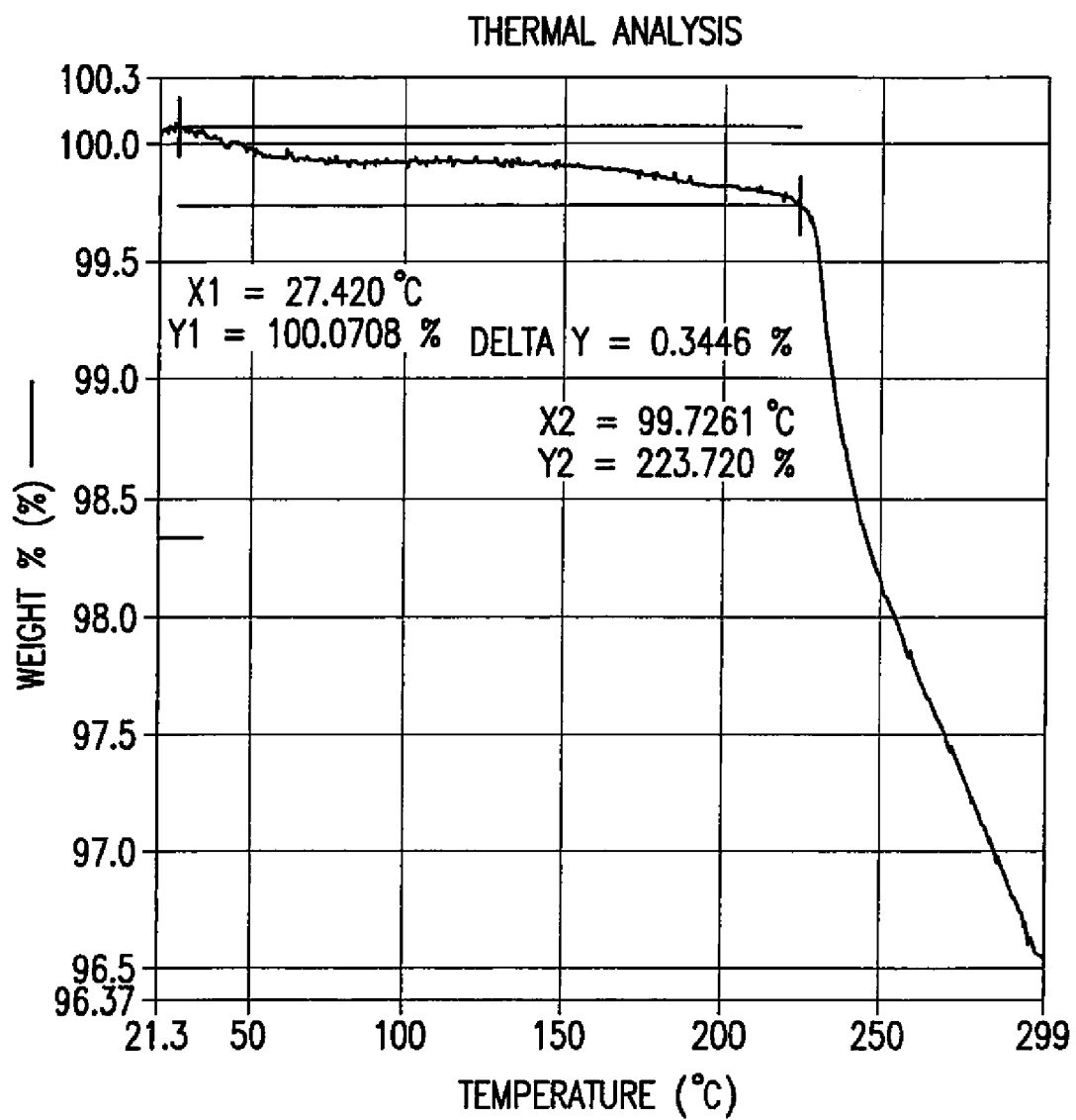
FIG. 16: presents a TGA thermogram of Form VII.

Thermogravimetric analysis was carried out using a Perkin Elmer TGA-7 system with $N_2$ flow. The sample was heated from 20 C. to 300 C. at 10 C./min. The weight was calibrated with indium and a standard 20 mg weight. A TG curve for Form VII is shown is FIG. 16. TGA analysis showed a weight loss of 0.34%.

XRPD Pattern

Figure 17:
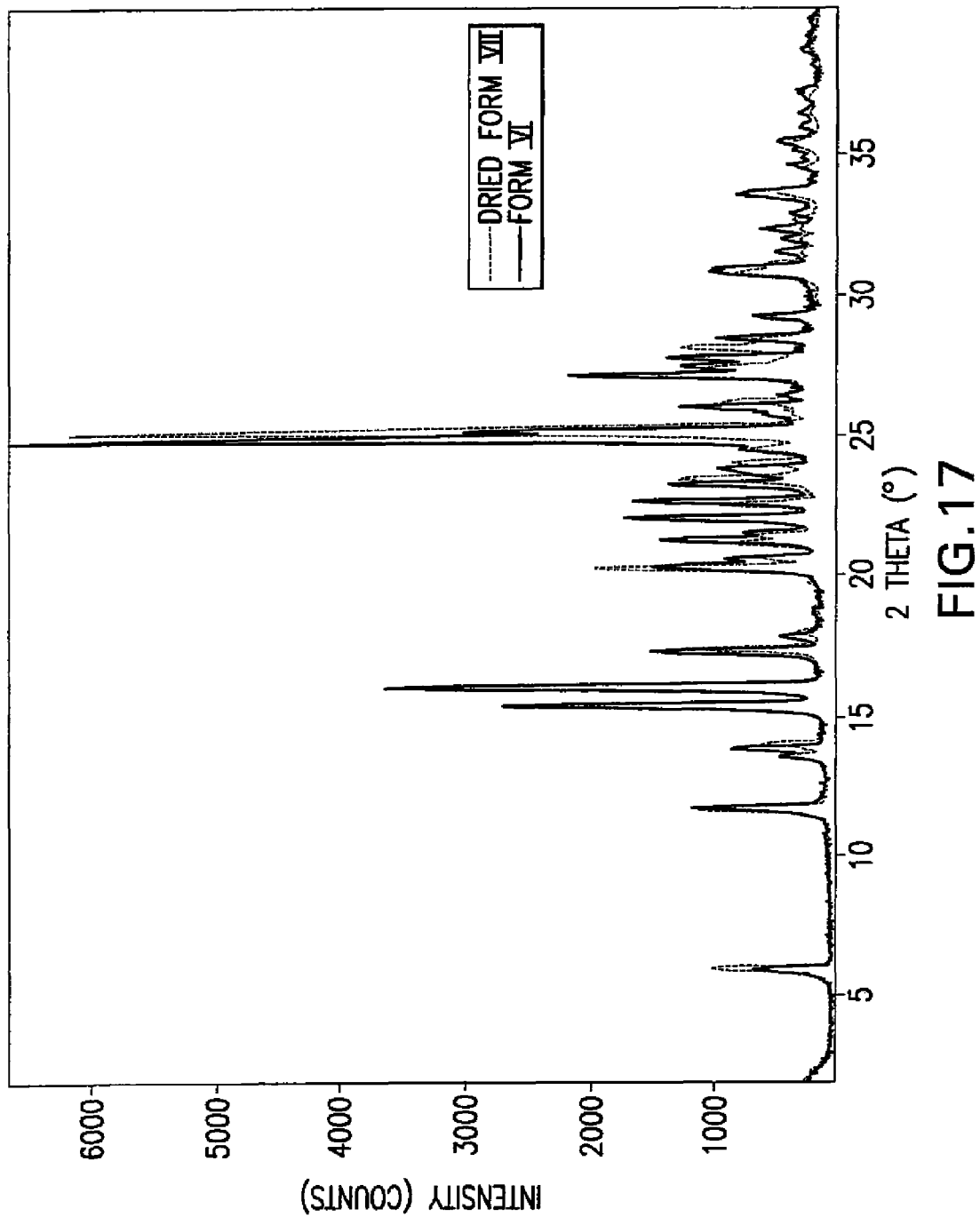
FIG. 17: presents XRPD diffractograms for Form VII.

XRPD pattern was obtained on a Philips XPert Pro instrument operating at 40 kV and 45 mA. A spinning sample holder was used. The peak positions were calibrated with a Si reference sample. The XRPD pattern of Form VII is shown in FIG. 17 and is different from that of the Form VI hemihydrate. The characteristic peaks corresponding to Form VII are 14.0, 17.4, 25.2 and 28.1 degrees 2-theta.

Figure 8:
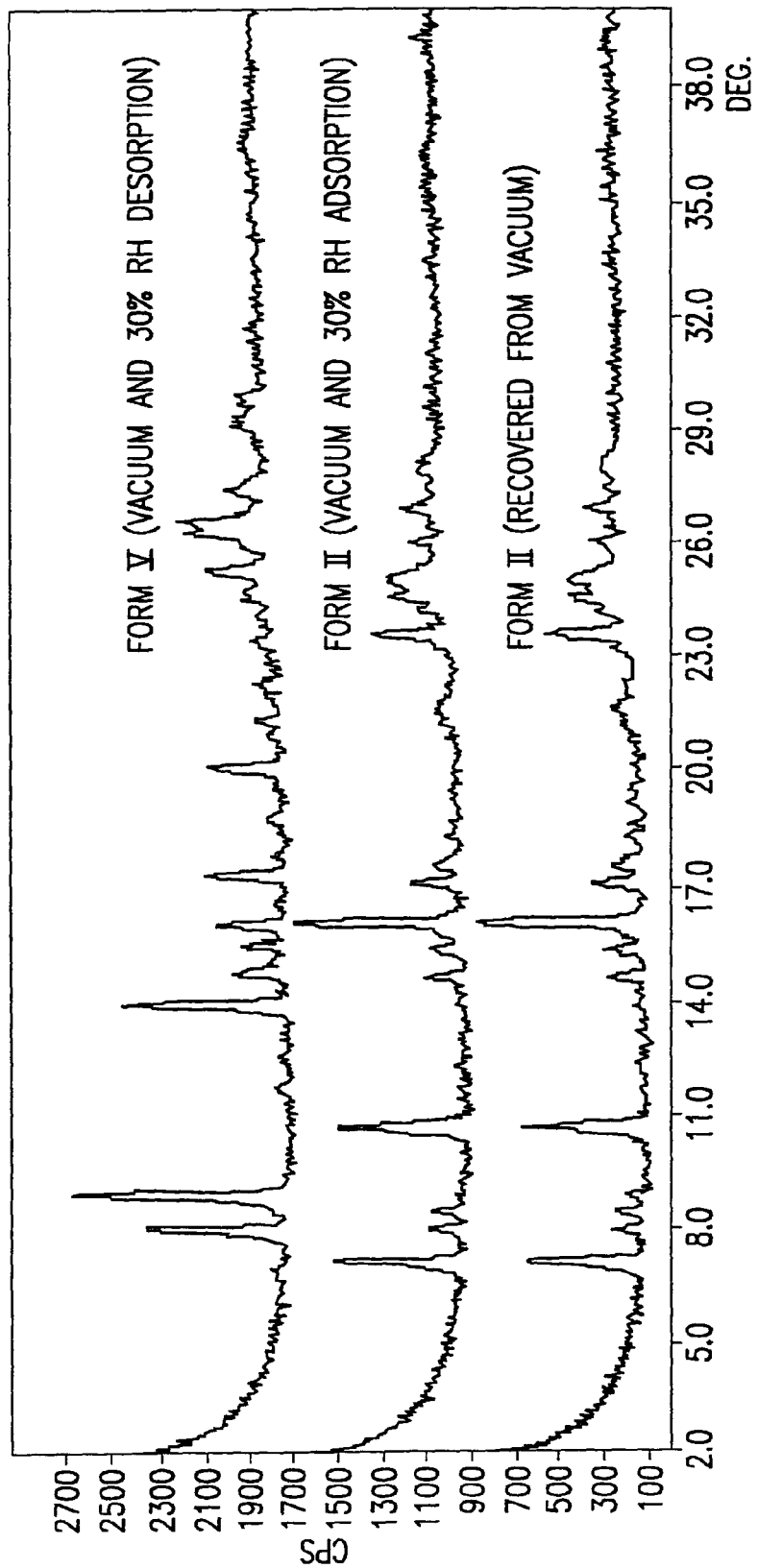
FIG. 8: presents XRPD diffractograms of products obtained upon drying Form V for 70 hours and at 30% adsorption and 30% desorption. The products are Form II and Form V.

Form I is non-hygroscopic with a maximum weight change of ca. 1% at 90% RH. On desorption, the tetrahydrate (Form IV) remains unchanged between 90-60% RH but converts to dihydrate (Form V) at 45-15% RH (FIG. 5 and FIG. 8).

Since the X-ray diffraction patterns of the dehydrated dihydrate and the hemihydrate are the same, we conclude that the hemihydrate is isostructural with the dehydrated dihydrate form obtained on drying in vacuo. To obtain the moisture sorption profile of the new anhydrous form obtained at the end of Adsorption 1/Desorption 1 in FIG. 5, the sample was kept in the dynamic moisture balance after the first adsorption/desorption experiment and a second adsorption/desorption experiment initiated under the same conditions. The dehydrated dihydrate, at the end of the first round adsorption/desorption studies, formed on drying at 0% RH, is hygroscopic and converts to a monohydrate at ca. 10-40% RH, adsorbing ca. 4% of water by weight. This observation is different from the adsorption behaviour in the first round adsorption/desorption profile where a hemihydrate (Form II) was formed between 10-40% RH. As with the hemihydrate (Form II), the monohydrate then converts to a tetrahydrate (Form IV) at 90% RH. Form IV remains unchanged at 90-60% RH but converts to the dihydrate (Form V) at 45-15% RH and to a dehydrated form upon drying at the end of the desorption experiment. Similar results obtained for both the adsorption 1/desorption 1 and adsorption 2/desorption 2 in replicate experiments.

Figure 9:
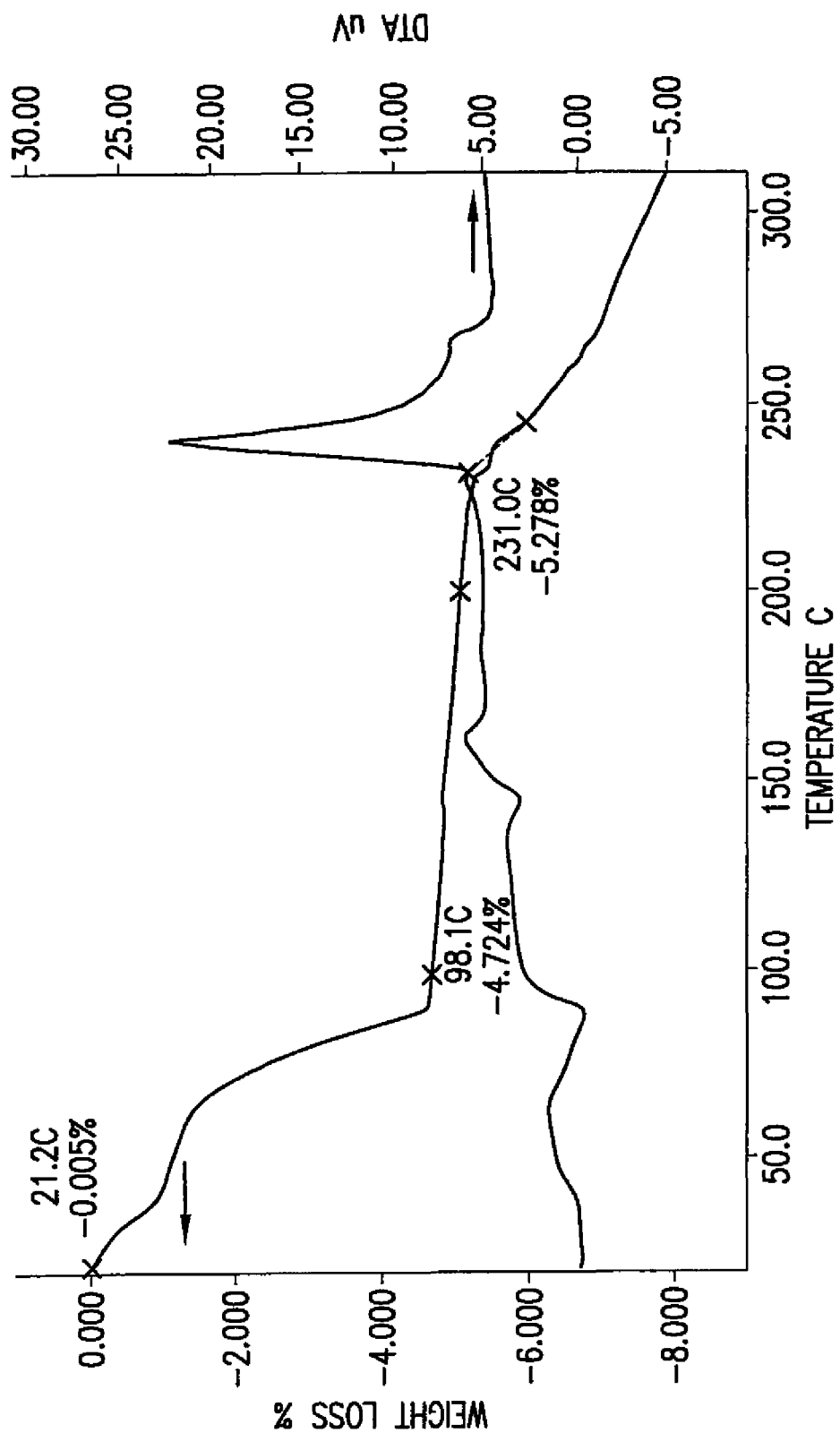
FIG. 9: presents a TGA thermogram of product obtained upon subjecting Form II to ambient humidity. The product is Form III.
Figure 10:
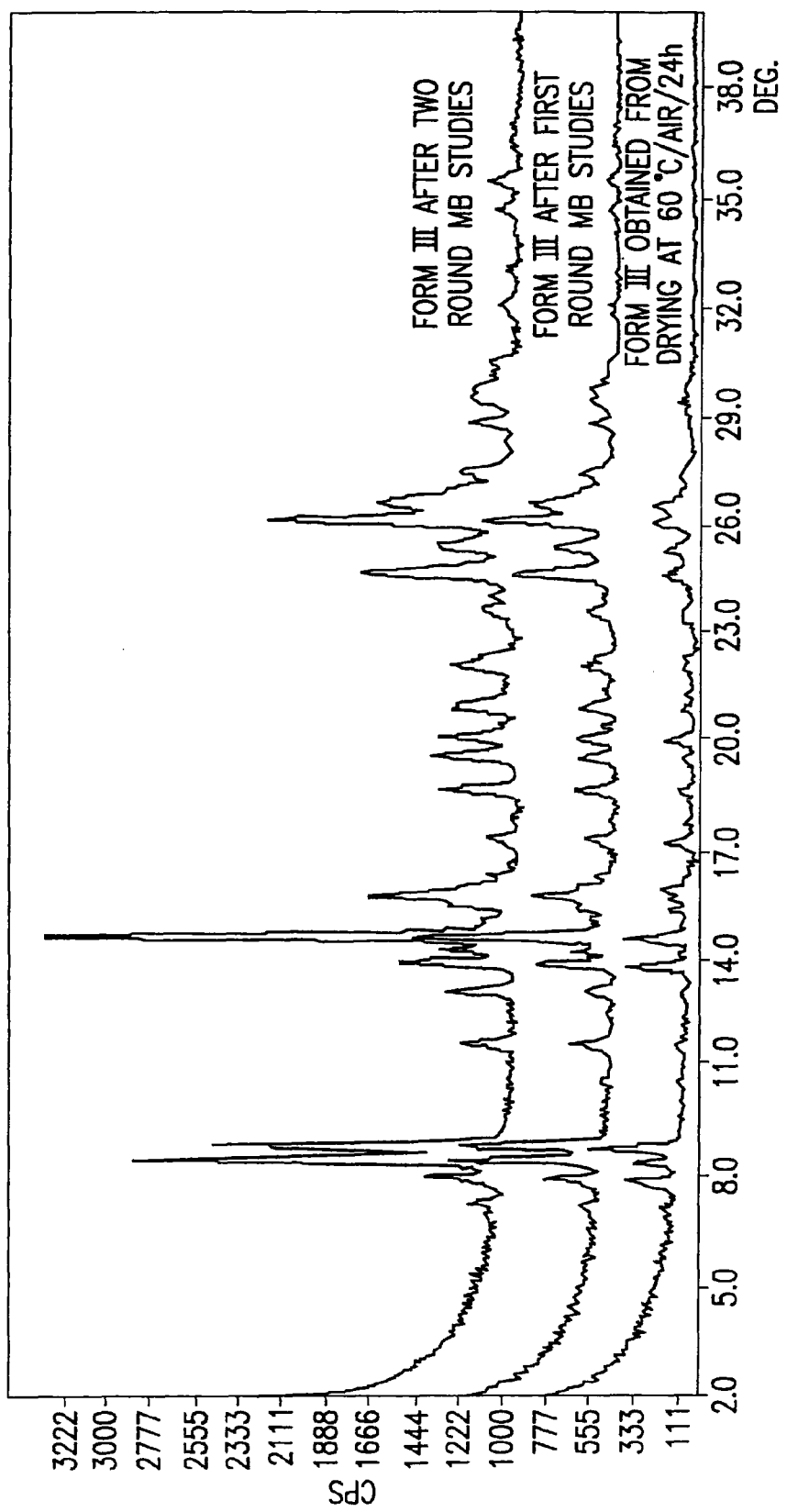
FIG. 10: presents XRPD diffractograms on product obtained upon subjecting Form II to ambient humidity. The product is Form III.

The dehydrated dihydrate (Form recovered from the two-round non-stop MB studies was evaluated by TGA and XRPD (FIG. 9 and FIG. 10). As can be seen by TGA, the compound forms a monohydrate under ambient humidity conditions (FIG. 9), a step-weight loss of about 4.7% occurs between 20-98° C. The XRPD pattern of this monohydrate is the same as that of sample recovered at the end of the first round of MB studies and to that obtained after drying at 60° C. in air (FIG. 10). The XRPD results shows that the crystalline reflections of the anhydrous forms obtained by dehydration of the dihydrate by temperature (60° C.) or after desorption at 0% RH readily convert to the monohydrate form (Form III) in air and the monohydrate form is more stable than anhydrous forms obtained on dehydration. A summary of the relative humidities under which the hydrates are formed is shown in Table 1.

TABLE 1

Compound IX hydrates and their relative humidities

| Crystal forms | RH % Conditions |
| --- | --- |
| Dehydrated dihydrate (Form II) | 2 hours drying at 0% RH under Vacuum |
| Hemihydrate (Form II) | ca. 10-40% RH on Adsorption 1* |
| Monohydrate (Form III) | ca. 10-40% RH on Adsorption 2* |
| Dihydrate (Form V) | ca. 45-15% RH on Desorption 1* and 2* |

TABLE 1-continued

Compound IX hydrates and their relative humidities

| Crystal forms | RH % Conditions |
| --- | --- |
| Tetrahydrate (Form IV) | ca. 75-90% RH on Adsorption 1* and ca. 90-60% RH on Desorption 1* and 2* |

*The number of 1 and 2 represents the first and second round adsorption/desorption processes, respectively.

Figure 11:
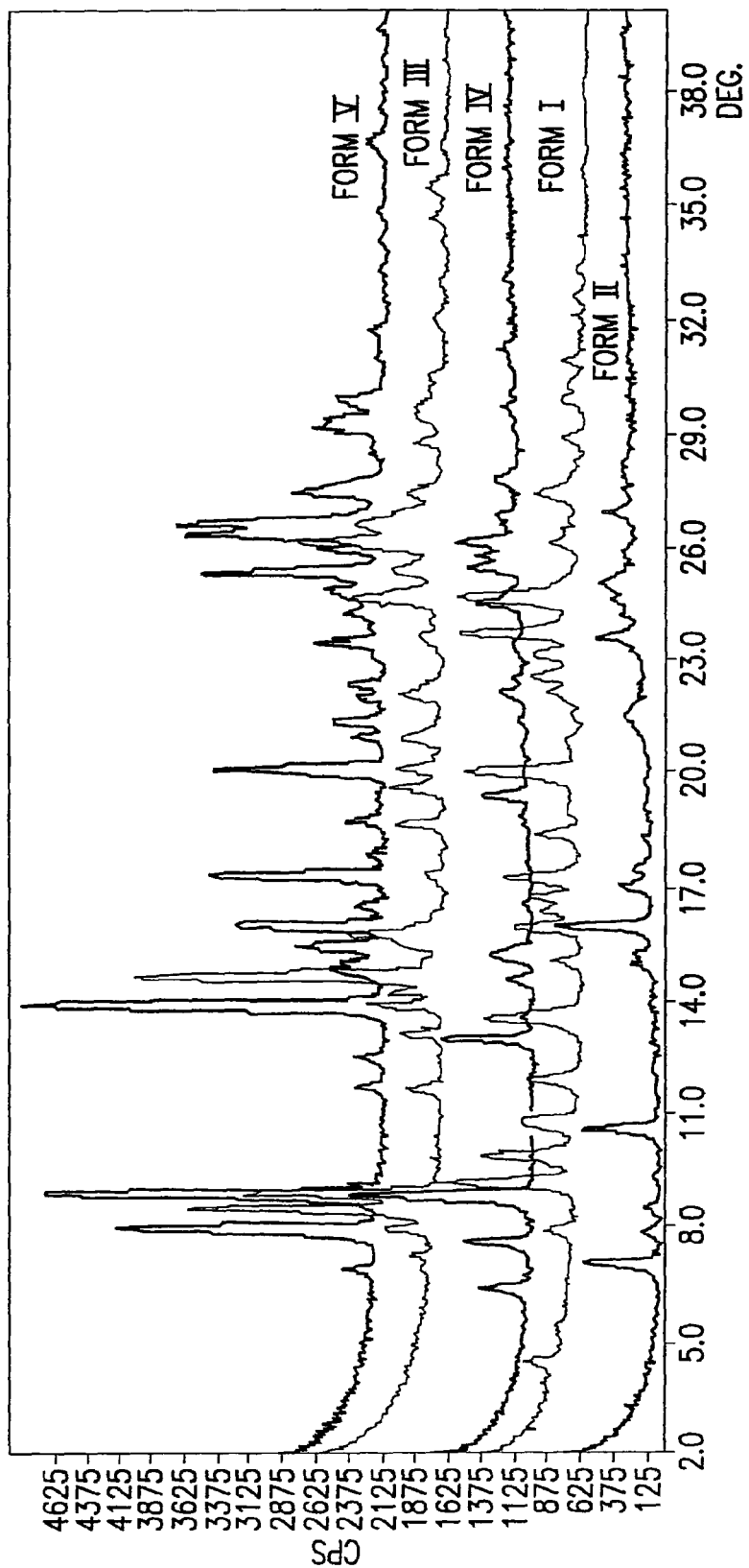
FIG. 11: presents XRPD diffractograms for Form I, Form II, Formal, Form N, and Form V.

The assignments are based on both the moisture sorption studies in the dynamic moisture balance and also moisture studies using the X-ray diffractometer. In summary, the X-ray powder diffractograms for Form I, Form II, Form IA Form IV and Form V are shown in FIG. 11. At least 4 characteristic reflection peaks were identified for each anhydrate and hydrate as shown in Table 2.

TABLE 2

XRPD Key Peak Listing for Compound IX Anhydrates and Hydrates

| Crystal forms | Peak* | Peak* | Peak* | Peak* | Peak* |
| --- | --- | --- | --- | --- | --- |
| Anhydrate (Form I) | 4.5 w | 9.2 s | 9.9 m | 10.9 m | 13.6 s |
| Dehydrated dihydrate (Form II) | 7.1 s | 8.6 w | 10.6 s | 17.1 w | |
| Hemihydrate (Form II) | 7.1 s | 8.6 w | 10.6 s | 17.1 w | |
| Monohydrate (Form III) | 8.5 s | 13.2 m | 14.7 s | 15.8 s | |
| Dihydrate (Form V) | 6.9 w | 12.6 w | 14.0 s | 17.4 s | |
| Tetrahydrate (Form IV) | 6.5 m | 7.7 m | 8.8 s | 13.0 s | |

*The unit for the peak position in the Table is in degrees 2θ. The relative intensities are given in w (weak), m (medium), s (strong)

In Summary:

The tetrahydrate (Form IV) obtained at elevated humidities and in direct contact with water is not stable and readily dehydrates to the dihydrate (Form V) between 15-45% RH. The XRPD pattern of this dihydrate was found to be different from the Compound IX (Form I). Form V readily dehydrates after 2 h in vacuo to an anhydrous crystal form (Form II) that is hygroscopic, followed by conversion to a hemihydrate (Form II) (10-40% RH) and to a tetrahydrate (Form IV)(75-90% RH) on adsorption, and then to a dihydrate (Form V) (45-15%) on desorption. The XRPD diffraction pattern of this dihydrate obtained on desorption was found to be the same as that of the dihydrate of Compound IX, recovered from water. The dehydrated dihydrate recovered at the end of MB studies was evaluated by TGA and XRPD. The dehydrated dihydrate converts to a monohydrate (Form III) under ambient humidity conditions. The XRPD pattern of this monohydrate is the same as that of sample recovered after drying at 60° C. in air, indicating that the dehydrated dihydrate forms recovered at the end of MB studies or after drying at 60° C. in air readily converts to a monohydrate. At least 4 characteristic peaks were identified for anhydrate and each hydrate, suggesting the existence of different crystal forms for anhydrate and each hydrate.

What is claimed is:

1. The hemihydrate of the compound IX

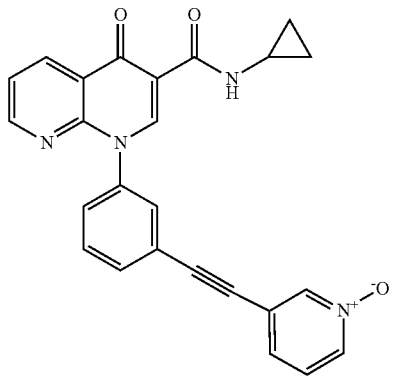

which is designated Form VI.

2. The Form VI, a hemihydrate of the compound IX, according to claim 1, wherein the Form VI has characteristic reflection peaks at 6.0, 15.3, 15.9, 23.8 and 25.0 degrees 2θ determined by x-ray powder diffraction.

3. A pharmaceutical composition comprising a non-toxic therapeutic amount of a Form VI, the hemihydrate, according to claim 1 and a pharmaceutically acceptable carrier.

* * * * *